United States Patent [19]

Su et al.

[11] Patent Number: 5,476,952

[45] Date of Patent: Dec. 19, 1995

[54] ANTITUMOR CYCLOPENTNAPHTHOQUINONE AND CYCLOPENTANTHRAQUINONE DERIVATIVES

[75] Inventors: Tsann-Long Su, Baldwin Place; Kyoichi A. Watanabe, Harrison; Tiang-Chao Chou, New York, all of N.Y.

[73] Assignee: Sloan-Kettering Institute for Cancer Research, New York, N.Y.

[21] Appl. No.: 30,581

[22] Filed: Mar. 12, 1993

[51] Int. Cl.$^6$ ............................................. C07D 203/26
[52] U.S. Cl. ............................................. 548/956; 548/961
[58] Field of Search ........................................ 548/956, 961

[56] References Cited

PUBLICATIONS

Moore, "Bioactivation as a Model for Drug Design Bioreductive Alkylation," Science, Aug., 1977; vol. 197, pp. 527–532.

Tomasz, et al., "Reductive Metabolism and Alkylating Activity of Mitomycin C Induced by Rat Liver Microsomes", Biochemistry, Aug., 1981; vol. 20, pp. 5056–5061.

Tomasz, et al., "Isolation and Structure of a Covalent Cross–Link Adduct Between Mitomycin C and DNA", Science, Mar., 1987, vol. 235, pp. 1204–1208.

Archer, "The Chemotherapy of Schistosomiasis", Ann. Rev. Pharmacol. Toxicology 1985; vol. 25, pp. 485–508.

Koyama, et al., "Intercalating Agents with Covalent Bond Forming Capability. A Novel Type of Potential Anticancer Agents. 2. Derivatives of Chrysophanol and Emodin", J. Med. Chem., Jul., 1989; vol. 32, pp. 1594–1599.

Brown, et al., "Studies on Compounds Related to Auxin–a and Auxin–b. Part III. The Preparation and Properties of the cycloPentenyl Analogue of Auxin–b Lactone", J. Chem. Soc., Nov., 1950; pp. 3634–3641.

Krow, et al., "A Simple Synthesis of 4–Cyclohexene–1, 2–cis–Diol and Its Use as the Precursor of a Functionalized Cyclohexanone Synthon", Org. Prepns. and Proceds. Int., Dec., 1977; vol. 9, pp. 285–288.

McCasland et al., "Synthesis of the Five Diastereomeric 1,2,4,5–Cyclohexanetetrols. Nuclear Magnetic Resonance Configurational Proofs", J. Org. Chem., Apr., 1963; vol. 28, pp. 894–900.

Caine et al., "Diels–Alder Reactions of 2–Carbomethoxy–4, 4–Dimethylcyclopentenone", Tetrahedron Lett., 1983; vol. 24, pp. 1353–1356.

Kinoshita et al., "Mitomycin Derivatives. 1. Preparation of Mitosane and Mitosene Compounds and their Biological Activies", J. Med. Chem., Feb., 1971; vol. 14, pp. 103–109.

Archer et al., "Preparation and Antischistosomal and Antitumor Activity of Hycanthone and Some of its Congeners. Evidence for the Mode of Action of Hycanthone", J. Med. Chem., Jan. 1988; vol. 31, pp. 254–260.

Primary Examiner—Jacqueline Haley
Attorney, Agent, or Firm—John P. White

[57] ABSTRACT

The present invention provides compounds having the structure:

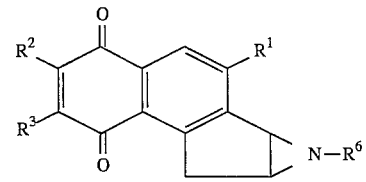

or having the structure:

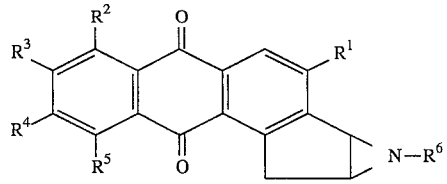

The present invention also provides a pharmaceutical compostion containing the compounds, methods of synthesizing the compounds, as well as methods of inhibiting growth of tumor cells and of treating a subject having a disease characterized by the proliferation of tumor cells.

3 Claims, No Drawings

ANTITUMOR CYCLOPENTNAPHTHOQUINONE AND CYCLOPENTANTHRAQUINONE DERIVATIVES

The invention described herein was made in the course of work under Grant Nos. CA-08748 and CA-18856 from the National Center Institute, National Institutes of Health, U.S. Department of Health and Human Services. The U.S. Government has certain rights in this invention.

BACKGROUND OF THE INVENTION

Throughout this application, various publications are referenced by Arabic numerals in parentheses. The disclosures of these publications in their entirety are hereby incorporated by reference into this application in order to more fully describe the state of the art as known to those skilled therein as of the date of the invention described and claimed herein.

Mitomycin-C (MC), an antineoplastic agent used in clinic for treatment of cancer has been the subject of chemical synthesis and modification due to its potent activity and intriguing chemical structure (1). This antibiotic is now known to act as a bifunctional alkylating agent that crosslinks to DNA, after a series of biotransformations (2). MC is able to bind covalently at the minor groove of DNA double strand forming interstrand cross-links at two diagonally opposed deoxyguanosine (dG) residues in a CpG or GpC sequence (3, 4).

Recently, Archer, et al., synthesized lucanthone and its derivatives, and found that these compounds exhibited potent antischistosomal and antitumor activity (5). They also reported that lucanthone is capable of intercalating into DNA and monoalkylating the DNA to give a covalently bound drug-DNA complex after bio-oxidation. More recently, it was found that the inactive natural products, chrysophanol and emodin, can be converted into potently active agents against certain tumor cell growth by addition of an akylating side chain functionality to the molecule (6), which would enable these compounds to intercalate into and then alkylate DNA. Although attempts have been made to develop antitumor agents possessing both alkylating and intercalating capabilities, development of synthetic intercalators with cross-linking potential and potential as antitumor agents is novel.

We have designed and synthesized cross-linking alkylating agents similar to MC and MC analogues with alkylation and intercalation potential. This specification describes the synthesis of derivatives of 2,3-dihydro-1H-benz[e]inden-4,9-dione(cyclopentnaphthoquinone) and 2,3-dihydro-1H-cyclopent[a]anthracene-6,11-dione(cyclopentanthraquinone), which bear both an alkylating side chain, such as a mustard or alkyl carbamate side-chain and an aziridine-ring. Both cyclopentnaphthoquinone and cyclopentanthraquinone derivatives, like MC, may undergo bio-reduction to the corresponding hydroquinones, which would make the C-3 position susceptible to nucleophilic attack by DNA by opening the aziridine ring. The alkylating function on C-4 would bind to another part of DNA resulting in the formation of a cross-linked DNA-drug conjugate. Compounds with hydroxymethyl carbamate (—$CH_2$—OCONR'R") group at C-4, like MC, would form active quinone methide, which would be also susceptible to nucleophilic attack by DNA, after elimination of HO—CONHR. These cyclopentanthraquinone derivatives, unlike MC, would intercalate into DNA, and, similar to MC, may cross-link with DNA. The chemical synthesis of the new MC analogues as well as their biological activities has not been reported to date.

SUMMARY OF THE INVENTION

The present invention provides a compound having the structure:

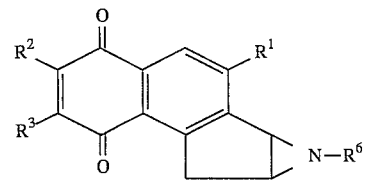

wherein $R^1$ is H, O—A or $CH_2$—O—A, wherein A is H or has the formula CONR'R" wherein R' and R" are the same or different and are hydrogen or a substituted or unsubstituted $C_1$–$C_6$ alkyl, aryl, cycloalkyl, or heterocyclic group; or A has the formula —M—NR'R" wherein R' and R" are the same or different and are hydrogen, or a $C_1$–$C_5$ alkyl, alkenyl, hydroxyalkyl, or haloalkyl group wherein the halo atom is fluorine, chlorine, bromine, or iodine atom; and —M— is an organic moiety having 1 to 10 carbon atoms and is a branched or straight chain alkyl, aryl, or cycloalkyl group, or has the structure:

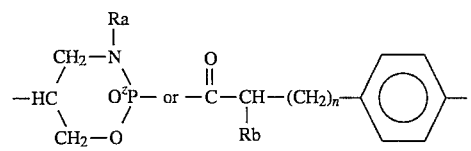

wherein n is 1 to 6, $R_a$ is H, or a $C_1$–$C_5$ haloalkyl group wherein the halo atom is F, Cl, Br, or I, and $R_b$ is H or $NH_2$;

$R^2$ and $R^3$ are the same or different and are hydrogen, cyano, or amino, a $C_1$–$C_5$ saturated or unsaturated, straight or branched chain alkyl group, alkylamino group, a $C_3$–$C_6$ cyclic alkylamino group, or an organic moiety having the structure:

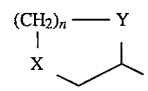

wherein n is 1 to 3 and X and Y are independently the same or different and are $CH_2$, O, S, N—R or P—R wherein R is H, or a $C_1$–$C_5$ alkyl or acyl group;

or having the structure:

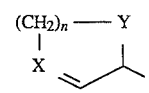

wherein n is 1 to 3, X is N, P or CH; and Y is $CH_2$, O, S, N—R or P—R wherein R is H, or a $C_1$–$C_5$ alkyl or acyl group;

or has the formula —O—M—NR'R" wherein R' and R" are independently the same or different and are hydrogen or a $C_1$–$C_5$ alkyl, alkenyl, hydroxyalkyl, or haloalkyl group wherein the halo atom is F, Cl, Br, or I, and —M— is an organic moiety having 1 to 10 carbon atoms and is a branched or straight chain alkyl, aryl, or cycloalkyl group, or has the structure:

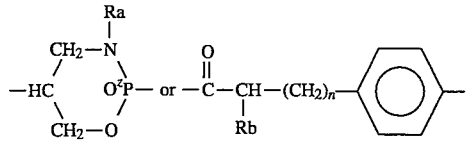

wherein n is 1 to 6, is H, or a $C_1$–$C_5$ haloalkyl group wherein the halo atom is F, Cl, Br, or I, and R is H or $NH_2$; and $R^6$ is hydrogen or a substituted or unsubstituted $C_1$–$C_9$ alkyl, aryl, or cycloalkyl group.

The present invention also provides a method of synthesizing a compound having the above-identified structure.

The present invention also provides a compound having the structure:

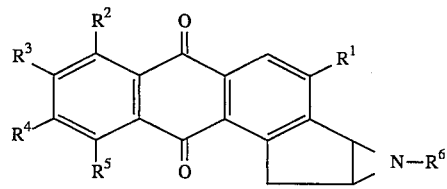

wherein $R^1$ is H, O—A or $CH_2$—O—A, wherein A is H or has the formula CONR'R" wherein R' and R" are the same or different and are hydrogen or a substituted or unsubstituted $C_1$–$C_6$ alkyl, aryl, cycloalkyl, or heterocyclic group; or A has the formula —M—NR'R" wherein R' and R" are the same or different and are hydrogen, or a $C_1$–$C_5$ alkyl, alkenyl, hydroxyalkyl, or haloalkyl group wherein the halo atom is a fluorine, chlorine, bromine, or iodine atom; and —M— is an organic moiety having 1 to 10 carbon atoms and is a branched or straight chain alkyl, aryl, or cycloalkyl group, or has the structure:

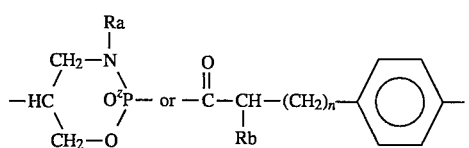

wherein n is 1 to 6, $R_a$ is H, or a $C_1$–$C_5$ haloalkyl group wherein the halo atom is F, Cl, Br, or I, and $R_b$ is H or $NH_2$;

$R^2$, $R^3$, $R^4$ and $R^5$ are the same or different and are hydrogen, cyano, or amino, a $C_1$–$C_5$, saturated or unsaturated, straight or branched chain alkyl group, alkylamino group, a $C_3$–$C_6$ cyclic alkylamino group, or an organic moiety having the structure:

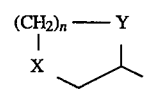

wherein n is 1 to 3 and X and Y are independently the same or different and are $CH_2O$, S, N—R or P—R wherein R is H, or a $C_1$–$C_5$ alkyl or acyl group;

or having the structure:

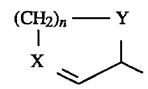

wherein n is 1 to 3, X is N, P or CH; and Y is $CH_2O$, S, N—R or P—R wherein R is H, or a $C_1$–$C_5$ alkyl or acyl group;

or has the formula —O—M—NR'R" wherein R' and R" are independently the same or different and are hydrogen or a $C_1$–$C_5$ alkyl, alkenyl, hydroxyalkyl, or haloalkyl wherein the halo atom is F, Cl, Br, or I, and —M— is an organic moiety having 1 to 10 carbon atoms and is a branched or straight chain alkyl, aryl, or cycloalkyl group, or has the structure:

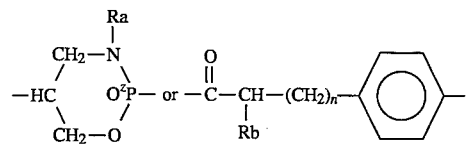

wherein n is 1 to 6, $R_a$ is H, or a $C_1$–$C_5$ haloalkyl group wherein the halo atom is F, Cl, Br, or I, and $R_b$ is H or $NH_2$; and $R^6$ is hydrogen or a substituted or unsubstituted $C_1$–$C_9$ alkyl, aryl, or cycloalkyl group.

The present invention also provides a method of synthesizing a compound having the above-identified structure.

The present invention further provides a pharmaceutical compostion which comprises an amount of either of the above-identified compounds and a pharmaceutically acceptable carrier.

The present invention also provides a method of inhibiting growth of tumor cells which comprises contacting the tumor cells with an effective tumor growth inhibiting amount of the above-identified compounds to thereby inhibit growth of tumor cells.

The present invention also provides a method of treating a subject having a disease characterized by the proliferation of tumor cells which comprises administering to the subject an effective tumor growth inhibiting amount of either of the above-identified compounds in a pharmaceutical composition effective to inhibit the growth of tumor cells.

Lastly, the present invention also provides a method of synthesizing, the above-identified compounds.

DETAILED DESCRIPTION OF THE INVENTION

The present invention provides a compound having the structure:

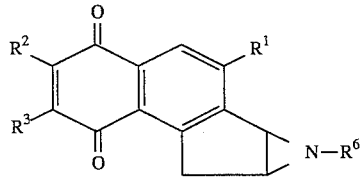

wherein

R[1] is H, O—A or CH$_2$—O—A, wherein A is H or has the formula CONR'R" wherein R' and R" are the same or different and are hydrogen or a substituted or unsubstituted C$_1$–C$_6$ alkyl, aryl, cycloalkyl, or heterocyclic group; or A has the formula —M—NR'R" wherein R' and R") are the same or different and are hydrogen, or a C$_1$–C$_5$ alkyl, alkenyl, hydroxyalkyl, or haloalkyl group wherein the halo atom is fluorine, chlorine, bromine, or iodine atom; and —M— is an organic moiety having 1 to 10 carbon atoms and is a branched or straight chain alkyl, aryl, or cycloalkyl group, or has the structure:

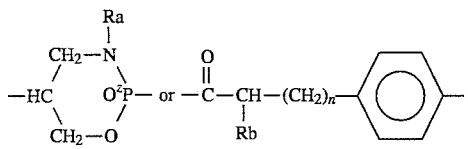

wherein n is 1 to 6, R$_a$ is H, or a C$_1$–C$_5$ haloalkyl group wherein the halo atom is F, Cl, Br, or I, and R$_b$ is H or NH$_2$;

R[2] and R[3] are the same or different and are hydrogen, cyano, or amino, a C$_1$–C$_5$ saturated or unsaturated, straight or branched chain alkyl group, alkylamino group, a C$_3$–C$_6$ cyclic alkylamino group, or an organic moiety having the structure:

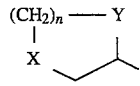

wherein n is 1 to 3 and X and Y are independently the same or different and are CH$_2$, O, S, N—R or P—R wherein R is H, or a C$_1$–C$_5$ alkyl or acyl group; or having the structure:

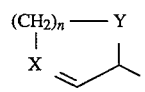

wherein n is 1 to 3, X is N, P or CH; and Y is CH$_2$O, S, N—R or P—R wherein R is H, or a C$_1$–C$_5$ alkyl or acyl group;

or has the formula —O—M—NR'R" wherein R' and R" are independently the same or different and are hydrogen or a C$_1$–C$_5$ alkyl, alkenyl, hydroxyalkyl, or haloalkyl group wherein the halo atom is F, Cl, Br, or I, and —M— is an organic moiety having 1 to 10 carbon atoms and is a branched or straight chain alkyl, aryl, or cycloalkyl group, or has the structure:

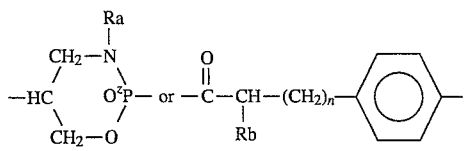

wherein n is 1 to 6, R$_a$ is H, or a C$_1$–C$_5$ haloalkyl group wherein the halo atom is F, Cl, Br, or I, and R$_b$ is H or NH$_2$; and R[6] is hydrogen or a substituted or unsubstituted C$_1$–C$_9$ alkyl, aryl, or cycloalkyl group.

Compounds having the above-identified structure, although not limited to the following compounds, may be selected from the group consisting of:

7-amino-2,3-aziridino-4-[2-bis(2-chloroethyl)amino]ethoxy-2,3-dihydro- 8-methyl-1H-benz[e]inden-6,9-dione, 7-amino-4-[2-bis(2-chloroethyl)amino]ethoxy-2,3-dihydro-8-methyl-2,3-N-methylaziridino-1H-benz[e]inden-6,9-dione, 7-amino-2,3-aziridino-4-[2-bis(2-hydroxyethyl)amino]ethoxy-2,3-dihydro- 8-methyl-1H-benz[e]inden-6,9-dione, 2,3-aziridino-4-[2 -bis(2-chloroethyl)amino]ethoxy-2,3-dihydro-7-methoxy- 8-methyl-1H-benz[e]inden-6,9-dione, 4-[2-bis(2-chloroethyl)amino]ethoxy-2,3-dihydro-7-methoxy- 8-methyl-2,3-N-methylaziridino-1H-benz[e]inden-6,9-dione, 2,3-aziridino-4-[2-bis(2-chloroethyl) amino]ethoxy-7-cyano-2,3-dihydro- 8 -methyl-1H-benz[e]inden-6,9-dione, 2,3-aziridino-4-[2-bis(2-chloroethyl)amino]ethoxy-2,3-dihydro-7-ethyleneimino- 8-methyl-1H-benz[e]inden-6,9-dione, 2,3-aziridino-4-[2-bis(2-chloroethyl)amino]ethoxy-2,3-dihydro-7-propargylamino-8 -methyl-1H-benz[e]inden-6, 9-dione, 2,3-aziridino-4-[2-bis(2-chloroethyl)amino]ethoxy-2,3-dihydro-7-tetrafurfurylamino- 8-methyl-1H-benz[e]inden-6,9-dione, 7-amino-2,3-aziridino-4-hydroxymethyl-2,3-dihydro-8-methyl- 1H-benz[e]inden-6,9-dione carbamate, 7-amino-2,3-aziridino-4-hydroxymethyl-2,3-dihydro-8-methyl-1H-benz[e]inden- 6,9-dione N-methylcarbamate, 7-amino-2,3-dihydro-4-hydroxymethyl-8-methyl-2,3-N-methylaziridino- 1H-benz[e]inden-6,9-dionecarbamate, 7-amino-2,3-dihydro-4-hydroxymethyl-8-methyl-2,3-N-methylaziridino- 1H-benz[e]inden-6,9-dione N-methylcarbamate, 2,3-aziridino-2,3-dihydro-4-hydroxymethyl-7-methoxy-8-methyl- 1H-benz[e]inden-6,9-dione carbamate, 2,3-aziridino-2,3-dihydro-4-hydroxymethyl-7-methoxy-8-methyl- 1H-benz[e]inden-6,9-dione N-methylcarbamate, 2,3-dihydro-4-hydroxymethyl-7-methoxy-8-methyl-2,3-N-methyl-aziridino- 1H-benz[e]inden-6,9-dione, 2,3-aziridino-7-cyano-2,3-dihydro-4-hydroxymethyl-8-methyl- 1H-benz[e]inden-6,9-dione carbamate, 2,3-aziridino-2,3-dihydro-4-hydroxymethyl-7-ethyleneimino- 8-methyl-1H-benz[e]inden-6,9-dione carbamate, 2,3-aziridino-2,3-dihydro-4-hydroxymethyl-7-propargylamino- 8-methyl-1H-benz[e]inden-6,9-dione carbamate, and 2,3-aziridino-2,3-dihydro-4-hydroxymethyl-7-tetrafurfurylamino- 8-methyl-1H-benz[e]inden-6,9-dione carbamate.

Compounds having the above-identified structure can be synthesized by the following method:

a) contacting a substituted or unsubstituted benzoquinone with a compound having the structure:

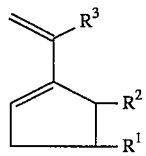

wherein $R^1$ and $R^2$ are the same or different and are hydrogen, or a $C_1$–$C_5$ O-alkyloxymethyl, O-aryloxymethyl, O-acyl, O-aroyl, isopropylidenedioxy, carbonyldioxy, or O-silyl group; and $R^3$ is hydrogen, hydroxy, O-acyl, O-aroyl, O-silyl or a $C_1$–$C_5$ alkyloxy or hydroxyalkyl group, or is —$CH_2R^4$ wherein $R^4$ is hydroxy, benzyloxy, phenylthio, or a $C_1$–$C_5$ alkyloxymethoxy, O-aryloxymethoxy, O-acyl, O-aroyl, or O-silyl group;

under Dieis-Alder conditions, followed by treatment with a dehydrogenating agent to form a compound having the structure:

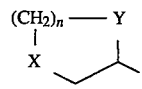

wherein $R^1$, $R^2$ and $R^3$ are the same as defined previously; and $R^5$ and $R^6$ are the same or different and are hydrogen, cyano, amino, a $C_1$–$C_5$ saturated or unsaturated, straight or branched chain alkyl group, alkylamino group, a $C_3$–$C_6$ cyclic alkylamino group, or an organic moiety having the structure:

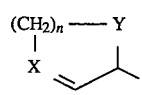

wherein n is 1 to 3 and X and Y are independently the same or different and are $CH_2$, O, S, N—R or P—R wherein R is H, or a $C_1$–$C_5$ alkyl or acyl group;

or having the structure:

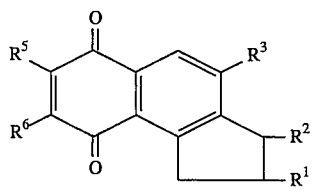

wherein n is 1 to 3, X is N, P or CH; and Y is $CH_2O$, S, N—R or P—R wherein R is H, or a $C_1$–$C_5$ alkyl or acyl group;

or have the formula —O—M—NR'R" wherein R' and R" are independently the same or different and are $C_1$–$C_5$ alkyl, alkenyl, hydroxyalkyl, or haloalkyl wherein the halo atom is F, Cl, Br, or I, and —M— is an organic moiety having 1 to 10 carbon atoms and is a linear or branched chain alkyl, aryl, or cycloalkyl group, or has the structure:

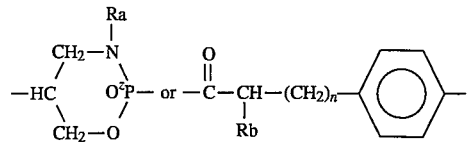

wherein n is 1 to 6, $R_a$ is H or a $C_1$–$C_5$ haloalkyl group wherein the halo atom is F, Cl, Br, or I and $R_b$ is H or $NH_2$;

b) treating the compound formed in step (a) under hydrolysis conditions allowing for selective removal of the $R^3$ protecting group to form a compound having the structure:

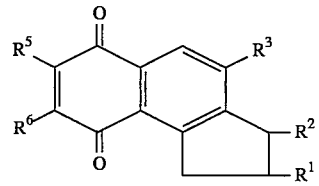

wherein $R^3$ is OH or $CH_2OH$; and
$R^1$, $R^2$, $R^5$, and $R^6$ are the same as defined in step (a);

c) treating the compound formed in step (b) with a halocarbamate having the formula X—CONR'R" wherein X is F, Cl, Br or I; and R' and R" are the same or different and are hydrogen or a substituted or unsubstituted $C_1$–$C_6$ alkyl, aryl, or cycloalkyl group; or treating with an alkylhalide having the formula X—M—NR'R" wherein X is F, Cl, Br, or I; R' and R" are the same or different and are hydrogen, or a $C_1$–$C_5$ alkyl, alkenyl, hydroxyalkyl, or a $C_1$–$C_5$ haloalkyl group wherein the halo atom is a fluorine, chlorine, bromine, or iodine atom; and —M— is an organic moiety having 1 to 10 carbon atoms and is a branched or straight chain alkyl, aryl, cycloalkyl, or has the structure:

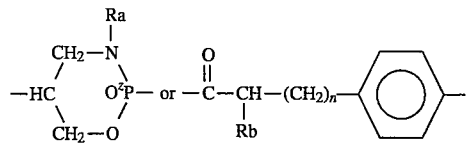

wherein n is 1 to 6, $R_a$ is H or a $C_1$–$C_5$ haloalkyl group wherein the halo atom is F, Cl, Br, or I and is H or $NH_2$;

to form a compound having the structure:

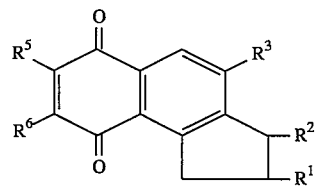

wherein $R^1$, $R^2$, $R^5$, and $R^6$, are the same as defined step (b); and

R3 is O—A or CH$_2$—O—A, wherein A has the formula CONR'R" wherein R' and R" are the same or different and are hydrogen or a substituted or unsubstituted C$_1$-C$_6$ alkyl, aryl, or cycloalkyl group; or A has the formula —M—NR'R" wherein R' and R" are the same or different and are hydrogen, or a C$_1$-C$_5$ alkyl, alkenyl, hydroxyalkyl, or haloalkyl group wherein the halo atom is a fluorine, chlorine, bromine, or iodine atom; and —M— is an organic moiety having 1 to 10 carbon atoms and is a linear or branched chain alkyl, aryl, or cycloalkyl group, or has the structure:

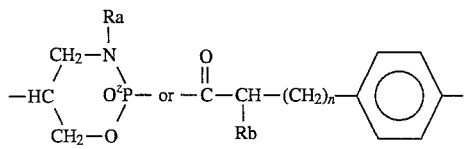

wherein n is 1 to 6, R$_a$ is H or a C$_1$-C$_5$ haloalkyl group wherein the halo atom is F, Cl, Br, or I and R$_b$ is H or NH$_2$;

d) treating the compounds formed in step (c) under acidic conditions to remove the protecting groups of R$_1$ and R$^2$ and form a compound having the structure:

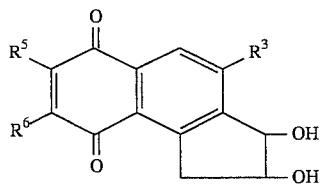

wherein R$^3$, R$^5$, and R$^6$, are the same as defined in step (c);

e) treating the compound formed in step (d) with an alkyl- or aryl-sulfonyl halide followed by treatment with an appropriate azide salt under such conditions to form a compound having the structure:

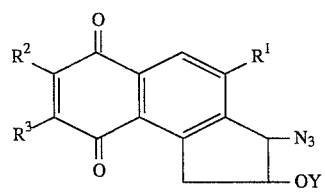

wherein Y is an alkyl- or aryl-sulfonyl group;
R$^1$ is O—A or CH$_2$—O—A, wherein A has the formula CONR'R" wherein R' and R" are the same or different and are hydrogen or a substituted or unsubstituted C$_1$-C$_6$ alkyl, aryl, or cycloalkyl group; or A has the formula M—NR'R" wherein R' and R" are the same or different and are hydrogen, or a C$_1$-C$_5$ alkyl, alkenyl, hydroxyalkyl, or haloalkyl group wherein the halo atom is a fluorine, chlorine, bromine, or iodine atom; and —M— is an organic moiety having 1 to 10 carbon atoms and is a linear or branched chain alkyl, aryl, or cycloalkyl group, or has the structure:

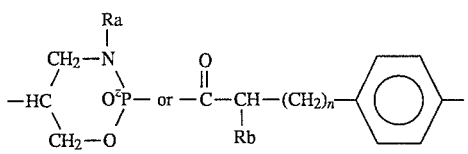

wherein n is 1 to 6, R$_a$ is H or a C$_1$-C$_5$ haloalkyl group wherein the halo is a fluorine, chlorine bromine or iodine and is R$_b$ H or NH$_2$; and R$^2$ and R$^3$ are the same or different and are hydrogen, cyano, or amino, a C$_1$-C$_5$ saturated or unsaturated, straight or branched chain alkyl group, alkylamino group, a C$_3$-C$_6$ cyclic alkylamino group, or an organic moiety having the structure:

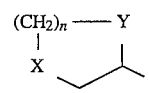

wherein n is 1 to 3 and X and Y are independently the same or different and are CH$_2$, O, S, N—R or P—R wherein R is H, C$_1$-C$_5$ alkyl, or acyl;
or having the structure:

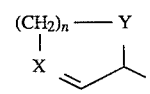

wherein n is i to 3, X is N, P or CH; and Y is CH$_2$O, S, or N—R or P—R wherein R is H, or a C$_1$-C$_5$ alkyl or acyl group;
or have the formula —O—M—NR'R" wherein R' and R" are independently the same or different and are C$_1$-C$_5$ alkyl, alkenyl, hydroxyalkyl, or haloalkyl group wherein the halo atom is F, Cl, Br, or I, and —M— is an organic moiety having 1 to 10 carbon atoms and is a branched or straight chain alkyl, aryl, or cycloalkyl group, or has the structure:

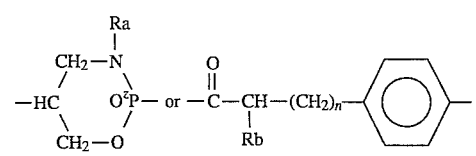

wherein n is 1 to 6, R$_a$ is H or C$_1$-C$_5$ haloalkyl group wherein the halo atom is F, Cl, Br, or I and is H or NH$_2$; and f) treating the compound formed in step (e) under reductive cyclization conditions followed by reaction with an acid halide or with the corresponding substituted or unsubstituted C$_1$-C$_9$ alkyl-, aryl-, or cycloalkyl halide to form a compound having the structure:

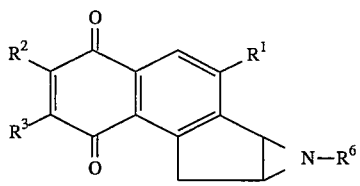

wherein $R^1$, $R^2$ and $R^3$ are the same as defined in step (e); and $R^6$ is hydrogen or a substituted or unsubstituted $C_1-C_9$ alkyl, aryl, or cycloalkyl group.

The present invention also provides a compound having the structure:

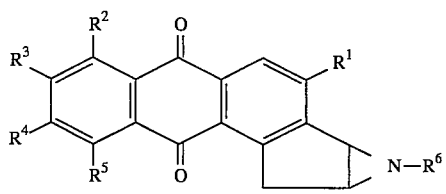

wherein $R^1$ is H, O—A or $CH_2$—O—A, wherein A is H or has the formula CONR'R" wherein R' and R" are the same or different and are hydrogen or a substituted or unsubstituted $C_1-C_6$ alkyl, aryl, cycloalkyl, or heterocyclic group; or A has the formula —M—NR'R" wherein R' and R" are the same or different and are hydrogen, or a $C_1-C_5$ alkyl, alkenyl, hydroxyalkyl, or haloalkyl group wherein the halo atom is a fluorine, chlorine, bromine, or iodine atom; and —M— is an organic moiety having 1 to 10 carbon atoms and is a branched or straight chain alkyl, aryl, or cycloalkyl group, or has the structure:

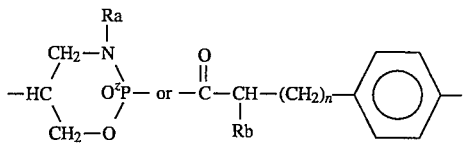

wherein n is 1 to 6, $R_a$ is H, or a $C_1-C_5$ haloalkyl group wherein the halo atom is F, Cl, Br, or I, and is H or $NH_2$;

$R^2$, $R^3$, $R_4$ and $R^5$ are the same or different and are hydrogen, cyano, or amino, a $C_1-C_5$, saturated or unsaturated, straight or branched chain alkyl group, alkylamino group, a $C_3-C_6$ cyclic alkylamino group, or an organic moiety having the structure:

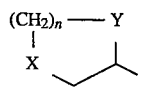

wherein n is 1 to 3 and X and Y are independently the same or different and are $CH_2$, O, S, N—R or P—R wherein R is H, or a $C_1-C_5$ alkyl or acyl group;

or having the structure:

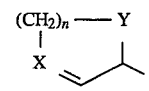

wherein n is 1 to 3, X is N, P or CH; and Y is $CH_2$, O, S, N—R or P—R wherein R is H, or a $C_1-C_5$ alkyl or acyl group;

or has the formula —O—M—NR'R" wherein R' and R" are independently the same or different and are hydrogen or a $C_1-C_5$ alkyl, alkenyl, hydroxyalkyl, or haloalkyl wherein the halo atom is F, Cl, Br, or I, and —M— is an organic moiety having 1 to 10 carbon atoms and is a branched or straight chain alkyl, aryl, or cycloalkyl group, or has the structure:

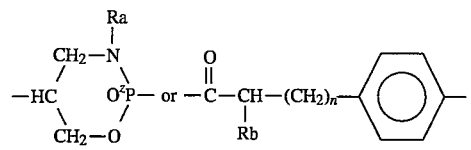

wherein n is 1 to 6, $R_a$ is H, or a $C_1-C_5$ haloalkyl group wherein the halo atom is F, Cl, Br, or I, and $R_b$ is H or $NH_2$; and $R^6$ is hydrogen or a substituted or unsubstituted $C_1-C_9$ alkyl, aryl, or cycloalkyl group.

Compounds having the above-identified structure, although not limited to the following compounds, may be selected from the group consisting of:

2,3-aziridino-4-[2-bis(2-chloroethyl)amino]ethoxy-2,3-dihydro- 1H-cyclopent[a]anthracene-6,11-dione, 4-[2-bis(2-chloroethyl)amino]ethoxy-2,3-dihydro-1H- 2,3-N-methylaziridino-cyclopent[a]anthracene-6,11-dione, 2,3-aziridino-4-[2-bis(2-chloroethyl)amino]ethoxy-2,3-dihydro- 7-methoxy-1H-cyclopent[a]anthracene-6,11-dione, 4-[2-bis(2-chloroethyl)amino]ethoxy-2,3-dihydro-7-methoxy- 2,3-N-methylaziridino-1H-cyclopent[a]-anthracene-6,11-dione, 2,3-aziridino-4-[2-bis(2-chloroethyl)amino]ethoxy-2,3-dihydro- 8-methoxy-1H-cyclopent[a]anthracene-6,11-dione, 2,3-aziridino-4-[2-bis(2-chloroethyl)amino]ethoxy-2,3-dihydro- 9-methoxy-1H-cyclopent[a]anthracene-6,11-dione, 2,3-aziridino-7-[2-bis(2-chloroethyl)amino]ethoxy-2,3-dihydro- 1H-cyclopent[a]anthracene-6,11-dione, 7-[2-bis(2-chloroethyl)amino]ethoxy-2,3-dihydro-1H- 2,3-N-methylaziridino-cyclopent[a]anthracene-6,11-dione, 2,3-aziridino-8-[2-bis(2-chloroethyl)amino]ethoxy-2,3-dihydro- 1H-cyclopent[a]anthracene-6,11-dione, 2,3-aziridino-9-[2-bis(2-chloroethyl)amino]ethoxy-2,3-dihydro- 1H-cyclopent[a]anthracene-6,11-dione, 2,3-aziridino-10-[2-bis(2-chloroethyl)amino]ethoxy-2,3-dihydro- 1H-cyclopent[a]anthracene-6,11-dione, 2,3-aziridino-4-[2-bis(2-hydroxyethyl)amino]ethoxy-2,3-dihydro- 1H-cyclopent[a]anthracene-6,11-dione, 2,3-aziridino-7-[2-bis(2-hydroxyethyl)amino]ethoxy-2,3-dihydro- 1H-cyclopent[a]anthracene-6,11-dione, 2,3-aziridino-8-[2-bis(2-hydroxyethyl)amino]ethoxy-2,3-dihydro- 1H-cyclopent[a]anthracene-6,11-dione, 2,3-aziridino-2,3-dihydro-4-hydroxymethyl- 1H-cyclopent[a]anthracene-6,11-dione carbamate, 2,3-aziridino-2,3-dihydro-4-hydroxymethyl- 1H-cyclopent [a]anthracene-6,11-dione-N-methylcarbamate,
2,3-dihydro-4-hydroxymethyl-2,3-N-methylaziridino- 1H-cyclopent[a]anthracene-6,11-dione carbamate,
2,3-aziridino-2,3-dihydro-4-hydroxymethyl-7-methoxy- 1H-cyclopent[a]anthracene-6,11-dione carbamate,
2,3-aziridino-2,3-dihydro-4-hydroxymethyl-8-methoxy- 1H-cyclopent[a]anthracene-6,11-dione carbamate,
2,3-aziridino-2,3-dihydro-4-hydroxymethyl-8-methoxy- 1H-cyclopent[a]anthracene-6,11-dione-N-methylcarbamate,
2,3-aziridino-2,3-dihydro-4-hydroxymethyl-9-methoxy- 1H-cyclopent[a]anthracene-6,11-dione carbamate,
2,3-dihydro-4-hydroxymethyl-10-methoxy-2,3-N-methylaziridino- 1H-cyclopent[a]anthracene-6,11-dione carbamate,
2,3-dihydro-4-hydroxymethyl-7-methoxy-2,3-N-methylaziridino- 1H-cyclopent[a]anthracene-6,11-dione carbamate,
2,3-dihydro-4-hydroxymethyl-7-methoxy-2,3-N-methylaziridino- 1H-cyclopent[a]anthracene-6,11-dione N-methylcarbamate,
2,3-dihydro-4-hydroxymethyl8-methoxy-2,3-N-methylaziridino- 1H-cyclopent[a]anthracene-6,11-dione carbamate, and
2,3-dihydro-4-hydroxymethyl-8-methoxy-2,3-N-methylaziridino- 1H-cyclopent[a]anthracene-6,11-dione N-methylcarbamate.

Compounds having the above-identified structure can be synthesized by the following method:

a) contacting a substituted or unsubstituted napthoquinone with a compound having the structure:

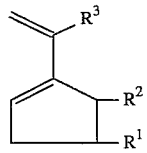

wherein $R^1$ and $R^2$ are the same or different and are hydrogen, or a $C_1$-$C_5$ O-alkyloxymethyl, O-aryloxymethyl, O-acyl, O-aroyl, isopropylidenedioxy, carbonyldioxy, or O-silyl group; and
$R^3$ is hydrogen, hydroxy, $C_1$-$C_5$ alkyloxy, $C_1$-$C_5$ hydroxyalkyl, O-acyl, O-aroyl, O-silyl or is —$CH_2R^4$ wherein $R^4$ is hydroxy benzyloxy phenylthio, or a $C_1$-$C_5$ alkyloxymethoxy, O-aryloxymethoxy, O-acyl, O-aroyl, or O-silyl group;

under Diels-Alder conditions, followed by treatment with a dehydrogenating agent to form a compound having the structure:

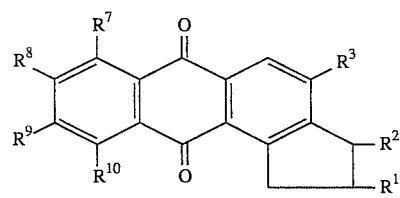

wherein $R^1$, $R^2$ and $R^3$ are the same as defined previously; and
$R^7$, $R^8$, $R^9$ and $R^{10}$ are the same or different and are hydrogen, cyano, or amino, a $C_1$-$C_5$ saturated or unsaturated, straight or branched chain alkyl group, alkylamino group, a $C_3$-$C_6$ cyclic alkylamino group, or an organic moiety having the structure:

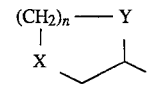

wherein n is 1 to 3 and X and Y are independently the same or different and are $CH_2$, O, S, N—R or P—R wherein R is H, or a $C_1$-$C_5$ alkyl or acyl group; or having the structure:

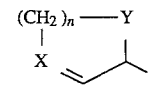

wherein n is 1 to 3, X is N, P or CH; and Y is $CH_2O$, S, N—R or P—R wherein R is H, or a $C_1$-$C_5$ alkyl or acyl group;
or has the formula —O—M—NR'R" wherein R' and R" are independently the same or different and are $C_1$-$C_5$ alkyl, alkenyl, hydroxyalkyl, or haloalkyl group wherein the halo atom is F, Cl, Br, or I, and —M— is an organic moiety having 1 to 10 carbon atoms and is a branched or straight chain alkyl, aryl, or cycloalkyl group, or has the structure:

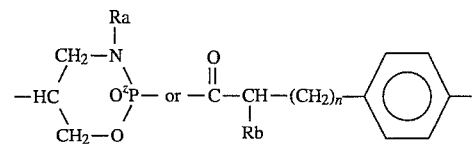

wherein n is 1 to 6, $R_a$ is H or a $C_1$-$C_5$ haloalkyl group wherein the halo atom is F, Cl, Br, or I and $R_b$ is H or $NH_2$;

b) treating the compound formed in step (a) under hydrolysis conditions allowing for selective removal of the $R^3$ protecting group to form a compound having the structure:

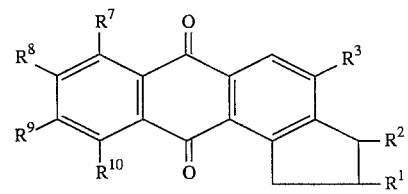

wherein $R^3$ is OH or $CH_2OH$; and
$R^1$, $R^2$, $R^7$, $R^8$, $R^9$ and $R^{10}$ are the same as defined in step (a);

c) treating the compound formed in step (b) with a halocarbamate having the formula X—CONR'R" wherein X is F, Cl, Br or I; and R' and R" are the same or different and are hydrogen or a substituted or unsubstituted $C_1$-$C_6$ alkyl, aryl, or cycloalkyl group; or treating with an alkylhalide having the formula X—M—NR'R" wherein X is F, Cl, Br, or I; R' and R" are the same or different and are hydrogen, or a $C_1$-$C_5$ s alkyl, alkenyl, hydroxyalkyl, or a $C_1$-$C_5$ haloalkyl group wherein the halo atom is a fluorine, chlorine, bromine, or iodine atom; and —M— is an orgainic moiety having 1 to 10 carbon atoms and is a branched or straight chain alkyl, aryl, or cycloalkyl group, or has the structure:

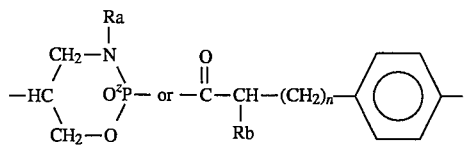

wherein n is 1 to 6, $R_a$ is H or a $C_1$–$C_5$ haloalkyl group wherein the halo atom is F, Cl, Br, or I and is H or $NH_2$;

to form a compound having the structure:

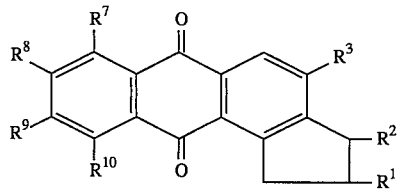

wherein $R^1$, $R^2$, $R^7$, $R^8$, $R^9$ and $R^{10}$ are the same as defined step (b); and $R^3$ is O—A or $CH_2$—O—A, wherein A has the formula CONR'R" wherein R' and R" are the same or different and are hydrogen or a substituted or unsubstituted $C_1$–$C_6$ alkyl, aryl, or cycloalkyl group; or A has the formula M—NR'R" wherein R' and R" are the same or different and are hydrogen, or a $C_1$–$C_5$ alkyl, alkenyl, hydroxyalkyl, or haloalkyl group wherein the halo atom is a fluorine, chlorine, bromine, or iodine atom; and —M— is an organic moiety having 1 to 10 carbon atoms and is a branched or straight chain alkyl, aryl, or cycloalkyl group, or has the structure:

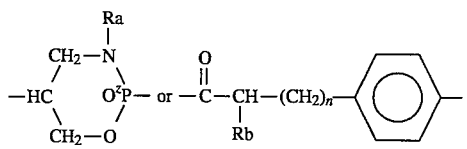

wherein n is 1 to 6, $R_a$ is H or a $C_1$–$C_5$ haloalkyl group wherein the halo atom is F, Cl, Br, or I and is H or $NH_2$;

d) treating the compounds formed in step (c) under acidic conditions to remove the protecting groups of $R^1$ and $R^2$ and form a compound having the structure:

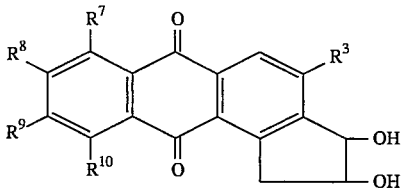

wherein $R^3$, $R^7$, $R^8$, $R^9$ and $R^{10}$ are the same as defined in step (c);

e) treating the compound formed in step (d) with an alkyl- or aryl-sulfonyl halide followed by treatment with an appropriate azide salt under such conditions to form a compound having the structure:

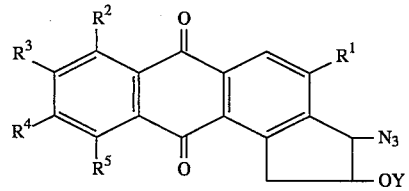

wherein Y is an alkyl- or aryl-sulfonyl group;

$R^1$ is O—A or $CH_2$—O—A, wherein A has the formula CONR'R" wherein R' and R" are the same or different and are hydrogen or a substituted or unsubstituted $C_1$–$C_6$ alkyl, aryl, or cycloalkyl group; or A has the formula —M—NR'R" wherein R' and R" are the same or different and are hydrogen, or a $C_1$–$C_5$ alkyl, alkenyl, hydroxyalkyl, or haloalkyl group wherein the halo atom is a fluorine, chlorine, bromine, or iodine atom; and —M— is an organic moiety having 1 to 10 carbon atoms and is a linear or branched chain alkyl, aryl, or cycloalkyl group, or has the structure:

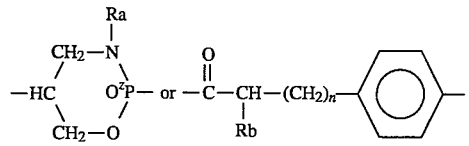

wherein n is 1 to 6, $R_a$ is H or a $C_1$–$C_5$ haloalkyl group wherein the halo atom is F, Cl, Br, or I and $R_b$ is H or $NH_2$; and $R^2$, $R^3$, $R^4$ and $R^5$ are the same or different and are hydrogen, cyano, or amino, a $C_1$–$C_5$ saturated or unsaturated, straight or branched chain alkyl group, alkylamino group, a $C_3$–$C_6$ cyclic alkylamino group, or an orgainic moiety having the structure:

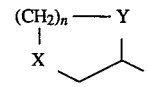

wherein n is 1 to 3 and X and Y are independently the same or different and are $CH_2O$, S, N—R or P—R wherein R is H, or a $C_1$–$C_5$ alkyl or acyl group;

or having the structure:

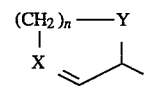

wherein n is 1 to 3, X is N, P or CH; and Y is $CH_2O$, S, N—R or P—R wherein R is H, or a $C_1$–$C_5$ alkyl or acyl group;

or have the formula —O—M—NR'R" wherein R' and R" are independently the same or different and are a $C_1$–$C_5$ alkyl, alkenyl, hydroxyalkyl, or haloalkyl group wherein the halo atom is F, Cl, Br, or I, and —M— is an organic moiety having 1 to 10 carbon atoms and is a branched or straight chain alkyl, aryl, or cycloalkyl group, or has the structure:

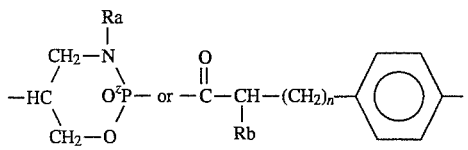

wherein n is 1 to 6, $R_a$ is H or a $C_1$–$C_5$ haloalkyl group wherein the halo atom is a fluorine, chlorine bromine or iodine and $R_b$ is H or $NH_2$; and f) treating the compound formed in step (e) under reductive cyclization conditions followed by reaction with an acid halide or the corresponding substituted or unsubstituted $C_1$–$C_9$ alkyl-, aryl-, or cycloalkylhalide to form a compound having the structure:

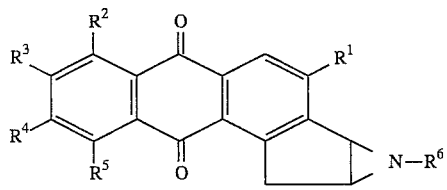

wherein $R^1$, $R^2$, $R^3$, $R^4$ and $R^5$ are the same as defined in step (e); and $R^6$ is hydrogen or a substituted or unsubstituted $C_1$–$C_9$ alkyl, aryl, or cycloalkyl group.

The present invention also provides a method of inhibiting the growth of tumor cells which comprises contacting the tumor cells with an effective tumor growth inhibiting amount of the compounds having the above-identified structures effective to inhibit growth of tumor cells.

As used herein, "an effective tumor growth inhibiting amount of the compound" is an amount of the compound which, when coming in contact with tumor cells, will inhibit or prevent the growth of the tumor cells.

In a preferred embodiment of the invention the compounds having the above identified structures are present in a pharmaceutical composition which comprises an amount of either of the compounds or a pharmaceutically acceptable salt thereof and a pharmaceutically acceptable carrier.

As used herein, the term "pharmaceutically acceptable carrier" encompasses any of the standard pharmaceutically accepted carriers, such as phosphate buffered saline solution, water, emulsions such as an oil/water emulsion, various types of wetting agents, tablets, coated tablets and capsules. Typically such carriers contain excipients such as starch, milk, sugar, certain types of clay, gelatin, stensic acid, talc, vegetable fats or oils, gums, glycols, or other known excipients. Such carriers may also include flavor and color additives or other ingredients.

In the practice of this invention the amount of the compound incorporated in the pharmaceutical composition may vary widely. Factors considered when determining the precise amount are well known to those skilled in the art. Examples of such factors include, but are not limited to, the subject being treated, the specific pharmaceutical carrier and route of administration being employed and the frequency with which the composition is to be administered.

The present invention also provides a method of treating a subject having a tumor which comprises administering to the subject an effective amount of the pharmaceutical composition, effective to inhibit the growth of tumor cells in the subject.

As used herein, "an effective amount of the pharmaceutical composition" is an amount of the pharmaceutical composition which contains an effective tumor growth controlling amount of the compound or pharmaceutically acceptable salt thereof, which, when combined with the pharmaceutically acceptable carrier will inhibit or prevent the growth of tumor cells but will be less than any amount which would cause a toxic reaction in the subject.

The present invention also provides a method of treating a subject having a disease characterized by the proliferation of tumor cells which comprises administering to the subject an effective amount of the pharmaceutical composition, effective to inhibit the growth of tumor cells.

Diseases against which the compounds of the present invention are useful include, but are not limited to, Hodgkin's disease, leukemias, lymphomas, gastric adenocarcinoma and carcinomas of the cervix, colon, rectum, pancreas, breast, bladder, head, neck, and lung and melanomas.

In the practice of this invention, the administration of the composition may be effected by any of the well known methods including, but not limited to, oral, intravenous, intraperitoneal, intramuscular or subcutaneous or topical administration. Topical administration can be effected by any method commonly known to those skilled in the art and include, but are not limited to, incorporation of the pharmaceutical composition into creams, ointments or transdermal patches.

The synthetic route for the preparation of compounds having the above-identified structures is the Dieis-Alder reaction of benzoquinones or naphthoquinones with a diene compound having the structure:

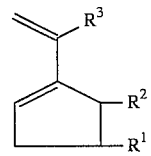

wherein $R^1$ and $R^2$ are the same or different and are hydrogen, or a $C_1$–$C_5$ O-alkyloxymethyl, O-aryloxymethyl, O-acyl, O-aroyl, isopropylidenedioxy, carbonyldioxy, or O-silyl group; and $R^3$ is hydrogen, hydroxy, $C_1$–$C_5$ alkyloxy, $C_1$–$C_5$ hydroxyalkyl O-acyl O-aroyl, O-silyl or is —$CH_2R^4$ wherein $R^4$ is hydroxy, benzyloxy, phenylthio, or a $C_1$–$C_5$ alkyloxymethoxy, O-aryloxymethoxy, O-acyl, O-aroyl, or O-silyl group;

The diene compound having the above structure, wherein $R^1$ is acetoxy or t-butyldimethylsilyoxy group and $R^2$ and $R^3$ are hydrogen, are prepared from the known 1-formylcyclopent-1-ene(7), which was synthesized from cyclohexane-1, 2-diol (available from Aldrich) via periodate oxidation and intramolecular Aldol condensation. The diene compound having the above structure wherein and are protected hydroxy functions, are either prepared from the known 1-cyclohexene-cis- 4,5-diol (8) or from the known cyclohexan-cis-1,2-trans- 4,5-tetrol (9), and are both synthesized from cyclohex-1,4-diene. The hydroxy functions of 1-cyclohexan-cis- 4,5-diol are protected by treatment with O-protecting agents such as acetic anhydride, trimethylsily chloride, tert-butyldimethylsily triflate and the like. The products are then converted into the O-protected 1-formyl-1-cyclopentene-4,5-diol via 1,2-diol formation using $OsO_4$, formic acid/$H_2O_2$, $KIO_3$/$I_2$/AcOH and the like, followed by oxidation using sodium periodate and intramolecular Aldol condensation. The O-protected 1-formly-1-cyclopentene-4,5-diol, for example, 1-formyl-4,5-isopropylidinedioxy-cyclopent-1-ene, is also synthesized from the known cyclohexan-cis-1,2-trans-4,5-tetrol (9). The tetrol is prepared in 84% yield by a modified procedure by oxidation of the known cyclohex-4-ene-cis-1,2-diol (8) with 95% formic acid and $H_2O_2$. After ketalization of the cyclohexan-cis-,2-trans-4,5-tetrol with 2,2-dimethoxypropane in DMSO in the presence of ion-exchange resin (Dowex 50w, $H^+$-form), the product, 4,5-isopropylidinedioxy-cyclohexan-1,2-diol, is treated with sodium periodate to form the 3,4-di-O-isopropylidine-3,4-dihydroxy-adipinaldehyde. An intramolecular Aldol reaction of the adipinaldehyde is performed by a modified method of Brown, et al. (7), by treatment with a mixture of piperidine/acetic acid (2:1 v/v) in toluene at 0° C., which gives 4,5-isopropylidinedioxy-1-formyl-cyclopent-1-ene in 53% yield.

The diene compound can also be synthesized as follows. Treatment of 1-formyl-cyclopent-1-ene, for example, 4,5-isopropylidinedioxy- 1-formyl-cyclopent-1-ene, with MeMgI affords 1-(4,5-isopropylidinedioxy-cyclopent-1-enyl)ethanol in 77% yield. Oxidation of 1-(4,5-isopropylidinedioxy-cyclopent-1-enyl)ethanol by treatment with an oxidizing agent such as $MnO_2$, $CrO_3$/pyridine/AcOH or the like, gives 1-acetyl- 4,5-isopropylidinedioxy-cyclopent-1-ene, which is converted into dienes, 1-acetoxy-1-(4,5-isopropylidinedioxy-cyclopent-1-ene)ethene or 1-(tert-butyldimethylsilyloxy)-1-(4,5-isopropylidinedioxy-cyclopent-1-ene)ethene in good yields via enol lithiate by treatment with LDA followed by acylation with $Ac_2O$ or silylation with TBDMS-triflate, respectively, by the known procedure (10) with slight modification.

The diene compound having the above structure wherein $R^3$ is $CH_2R^4$, wherein $R^4$ is a phenylthio group, is synthesized from the above 1-formyl-cyclopent-1-ene or the O-protected 1-formyl-cyclopent-1-ene-4,5-diol. 1-Formyl-cyclopent-1-ene is treated with lithiated thioanisol, and the product, 1-(cyclopent-1-enyl)-2-phenylthioethanol, is further converted into 2-(cyclopent-1-enyl)-3-phenylthio-prop-1-ene via oxidation to ketone using dichloro-dicyanabenzoquinone (DDQ), oxaylchloride/dimethylsulfoxide, $MnO_2$ or the like and diene formation using n-butyllithium/S-methyl-N-methyl-S-phenylsufoximine and Al/Hg).

The synthesis of the cyclopentnaphthoquinone and cyclopenanthraquinone compounds is further characterized as follows.

The contacting in the step (a) comprises the Dieis-Alder reaction of substituted benzoquinones or naphthoquinones with the diene compound to give their respective three-ring or four-ring products. The Dieis-Alder products are then converted into the corresponding cyclopentnaphthoquinones or cycyclopentanthraquinones by treatment with dehydrogenating agents, such as Pd/C, DDQ, $MnO_2$ or the like. Prolonged reaction of large excesses of benzoquinones or naphthoquinones with the diene compound will produce cyclopentbenzoquinones or cycyclopentanthraquinones, since the Dieis-Alder products are oxidized to form cyclopentbenzoquinones or cycyclopentanthraquinones by the excess of benzoquinones or naphthoquinones. For example, reaction of the diene compound wherein is an acetoxy group, $R^1$ and $R^2$ are an isopropylidinedioxy group, namely 1-acetoxy- 1-(4,5-isopropylidine-dioxy-cyclopent-1-enyl)ethene, with naphthoquinone, in a molar ratio of 1:2.5 in refluxing toluene for 1 day, gives 4-hydroxy-2,3-isoproylidinedoxycyclopent[a]anthracene- 6,11-dione in 95% yield.

In the preferred embodiment, the contacting in step (a) is performed in a solvent with a boiling point above 60° C., at a range of 60° C. to 160° C. for a period of from 1 hour to 2 days, but preferably one day. The solvent is benzene, toluene, xylene, diglyme and the like, but preferably toluene.

The molar ratio of the reactants in step (a) of the diene compound to benzoquinones or naphthoquinones can be 1 to 5, but is preferably 1 to 3.

Upon completion of the reaction in step (a), the mixture is cooled and the sovent is removed by evaporation in vacuo. The Dieis-Alder product can be isolated by recrystallization of the residue from alcohol such as methanol, ethanol and the like. The Dieis-Alder product can also be converted directly into the corresponding cyclopentbenzoquinone or cyclopentanthraquinones without isolation. The conversion of the Dieis-Alder product into cyclopentbenzoquinone or cyclopentanthraquinones is performed by treatment with dehydrogenating agent, such as Pd/C, DDQ, $MnO_2$ or the like, in a solvent with a boiling point above 100° C., at a temperature range of from 100° C. to 200° C. for a period of 1 hour to 2 days. The solvent is toluene, xylene, diglyme, diphenylether and the like. Preferably, the contacting is carried out at a temperature range of 100° C. to 150° C.

The treating in step (b) comprises the conversion of the compounds formed in step (a) to the corresponding 4-hydroxy substituted derivatives.

In one embodiment, the treating in step (b) comprises hydrolyzing the compounds formed in step (a), for example, wherein $R^3$ is acetoxy or tert-butyldimethylsilyloxy, by treatment with alkali such as ammonium hydroxide, triethylamine, potassium carbonate and the like, in water or in a mixture of water and alcohol, such as methanol, ethanol, propanol and the like, at a temperature range of from 25° C. to 100° C. for a period of 10 minutes to 5 hours, or with tetrabutylammonium fluoride in tetrahydrofuran, dioxane and the like, mixed with water or without water, at room temperature for a period of 5 minutes to 2 hours.

In another embodiment, the treating in step (b) comprises contacting the compounds formed in step (a) with cyanogen bromide to give derivative compounds wherein $R^3$ is —$CH_2R^4$, wherein $R^4$ is bromomethyl ($BrCH_2$), which are then hydrolyzed. For example, the compounds formed in step (a) are treated with cyanogen bromide in refluxing acetonitrile for 4.5 hours under nitrogen to give derivative compounds wherein $R^3$ is —$CH_2R^4$, wherein $R^4$ is bromomethyl ($BrCH_2$). The bromo derivative is treated with potassium acetate in dimethylformamide at 0° C. for 2.5 hours to afford the derivative compounds wherein $R^4$ is acetoxymethyl ($AcOCH_2$), which is then hydrolyzed to yield the compounds of step (b) by treatment with base such as sodium hydroxide, potassium hydroxide, sodium carbonate, sodium bicarboate, triethylamine, N,N-diethylaniline and the like.

The treating in step (c) comprises to O-alkylation of the compounds formed in step (b) to give the O-alkylated compounds.

In the preferred embodiment, the treating in step (c) comprises contacting the compounds formed in step (b) with an alkyl halide such as tris(2-chloro-ethyl)amine, 2-dimethylaminomethyl chloride, 2-diethylaminoethyl chloride and the like, in a mixture of base such as potassium carbonate in acetone, potassium carbonate in dimethylformamide, or sodium hydroxide in dimethylformamide. Preferably, the base is potassium carbonate in acetone.

In another embodiment, the treating in step (c) also comprises the carbamate formation of the compounds formed in step (b).

In this embodiment, the treating in step (c) comprises treating the compounds formed in step (b) with phenyl chlorocarbamate in pyridine in an ice-bath for a period of 30 minutes to 5 hours. After the reaction is complete, the mixture is diluted with water and extracted with chloroform. The chloroform extracts are combined and concentrated. The residue is dissolved in chloroform and then treated with ammonia under cooling in Dry Ice-acetone to give the carbamate (11). The methyl derivative carbamate is prepared by a procedure developed by Archer (12). Treatment of the compounds formed in step (b) with methylisocyanate in acetone at a temperature range of room temperature to 100° C., in period of 1 hour to 2 days affords the methyl carbamate derivatives.

The contacting in step (d) comprises the removing of the 2,3-O-protecting group of the compounds formed in steps (c) to give the corresponding 2,3-dihydroxy derivatives.

In the preferred embodiment, the treating in step (d) comprises contacting the compounds formed in step (c) with an acid such as hydrochloric acid, hydrobromic acid, sulfuric acid, formic acid, trifluoroacetic acid, or ion-exchange resin in acid form and the like, at a temperature range of −10° C. to 100° C., for a period of 10 minutes to 1 day. Preferrably, the treating in step (d) is performed in 80% trifluoroacetic acid in an ice-bath for 1 hour.

The contacting in step (e) comprises conversion of the compounds formed in step (d) into their corresponding 3-azidio-2-mesyl derivatives.

In the preferred embodiment, the treating in step (e) comprises contacting the compounds formed in step (d) with methanesulfonyl chloride, trifluoromethanesulfonyl chloride or toluenesulfonyl chloride in pyridine, triethylamine in chloroform or N,N-diethyl-aniline in methylenedichloride at a temperature range of −10° C. to 30° C., for a period of 20 minutes to 2 days. Upon completion of the reaction, the mixture is poured into ice-water and extracted with chloroform. The combined extracts are concentrated by evaporation in vacuo, and the residue is treated with sodium azide in dimethylsulfoxide or lithium azide in dimethylformamide at a temperature range of 0° C. to 50° C., for a period of 30 minutes to 1 day. The mixture is diluted with chloroform, washed with water, dried using $Na_2SO_4$ and evaporated to dryness. The products of step (e) are obtained either by recyrstallization or by chromatography.

The contacting in step (f) comprises the conversion of the compounds formed in step (e) into the corresponding 2,3-aziridine derivatives.

The conversion in step (f) comprises contacting the compounds formed in step (e) with triphenylphosphine in the presense of base such as sodium hydride or triethylamine, and the like, in tetrahydrofuran containing water or without water, at a temperature range of O° C. to 40° C. for a period of 30 minutes to 1 day. Upon the completion of the reaction, the mixture is washed with water, dried using $Na_2SO_4$ and evaporated in vacuo to dryness. The final product compounds of step (f) are obtained either by recrystallization of the solid residue, or by liquid column chromatography.

In the preferred embodiment of step (f) the compounds formed in step (e) are treated with triphenylphosphine and triethylamine in tetrahydrofuran containing a trace amount of water at room temperature for 1.5 hours. Treatment of the 2,3-aziridine derivatives with methyl iodide in refluxing acetone in the presence of potassium carbonate will form the corresponding N-methylaziridino derivatives.

The final product compounds formed in step (f) wherein $R^2$ is methoxy (MeO) at will react with various amines, such as liquid ammonia, dimethylamine, ethylamine, aziridine, aniline, and the like, to give various C-7 substituted amino derivatives by a known procedure.

The following Experimental Details section and Examples are set forth to aid in an understanding of the invention. These sections are not intended to, and should not be constructed to, limit in any way the invention set forth in the claims which follow thereafter.

EXPERIMENTAL DETAILS

EXAMPLE 1

4,5-Isopropylidenedioxy-cyclohexane-1,2-diol: A mixture of cyclohexane-1,2,4,5-tetrol (10 g, 7.6 mmol), Dowex 50W-X8 ($H^+$-form, 5 g) in DMSO (180 mL) and 2,2-dimethoxypropane (60 mL) is stirred at room temperature for 3 days, and then filtered through a pad of Celite. After removal of solvents in vacuo, the residue is chromotographed over a silica gel column (5×40 cm) using EtOAc as the eluent. 4,5-Isopropylidenedioxy-cyclohexan-1,2-diol is obtained as colorless cyrstals ($Et_2O$), 7.36 g (80%) with mp 110°–111° C. $^1H$ NMR ($D_2O$): δ1.34 and 1.50 (each 3H, s, 2×Me), 1.58–1.86 (2H, m, H-3, H-6), 2.02–2.43 (2H, m, H-3, H-6'), 3.40 (1H, ddd, H-4), 3.68 (1H, ddd, H-5), 4.20–4.40 (2H, m, H-1, H-2). Anal. Calc'd for $C_9H_{16}O_4$: C, 57.43; H, 8.57. Found: C, 57.38; H, 8.36.

By following the same procedure, the following compounds are prepared:
4,5-Dihydroxycarbonate-cyclohexan-1,2-diol,
4,5-ethylidenedioxy-cyclohexan-1,2-diol,
4,5-benzylidenedioxy-cyclohexan-1,2-diol,
4,5-(1-methoxyethylidenedioxy)-cyclohexan-1,2-diol, and
4,5-(α-methoxybenzylidenedioxy)-cyclohexan-1,2-diol.

EXAMPLE 2

3,4-Isopropylidenedioxy-adipinaldehyde: 1,2-Isopropylidenedioxy-cyclohexan-1,2-diol (5.0 g, 26.6 m mol) is added portionwise to a solution of $NaIO_4$ (6.9 g) in $H_2O$ (100 mL) at 0° C. The mixture is stirred at room temperature for 1 hour, and extracted with $CHCl_3$ (50 mL×15). The combined extracts are washed with $H_2O$, dried ($Na_2SO_4$), and concentrated in vacuo to give 4.91 g (99%) of crude 3,4-isopropylidendioxy-adipinaldehyde as a colorless liquid, which is sufficiently pure to be used directly in the next step. A small amount of pure sample can be obtained by chromatography on a silica gel column for analyses. $^1H$ NMR ($CDCl_3$): δ1.36 and 1.44 (each 3H, s, 2×Me), 2.34–2.88 (4H, m, 2×H-2 and 2×H-5), 4.60–4.83 (2H, m, H-3 and H-4), 9.76 (2H, dd, $J_{1,2a}=J_{5,6a}=1.9$ Hz, $J_{1,2b}=J_{5,6b}=1.4$ Hz, H-1, H-6). Anal. Calc'd for $C_9H_{14}O_4$: C, 58.05; H, 7.58. Found: C, 57.88; H, 7.40.

By following the same procedure, the following compounds are prepared:
4,5-Dihydroxycarbonate-adipinaldehyde,
4,5-ethylidenedioxy-adipinaldehyde,
4,5-benzylidenedioxy-adipinaldehyde,
4,5-(1-methoxyethylidenedioxy)-adipinaldehyde, and
4,5-(α-methoxybenzylidenedioxy)-adipinaldehyde.

EXAMPLE 3

1-Formyl-4,5-isopropylenedioxcyclopent-1-ene: A solution of 3,4-isopropylidenedioxy-adipinaldehyde (4.66 g, 25 mmol) in toluene (30 mL) is added dropwise to a solution of piperidine (1.16 mL) and AcOH (0.63 mL) in toluene (100 mL) in an ice bath. The reaction mixture is stirred at ambient temperature for 4 hours and then at room temperature for an additional 2 hours. The solution is washed successively with 10% NaHCO m aqueous solution, and $H_2O$, and extracted with EtOAc (50 mL×3). The combined extracts are washed with $H_2O$, dried ($Na_2SO_4$), and evaporated in vacuo to dryness. The residue is chromatographed over a silica gel column (3×40 cm, toluene/EtOAc, 2:1 v/v) to yield 1-Formyl-4,5-isopropylenedioxy-cyclopent-1-ene 2.25 g (54%) as a syrup, which crystallized on storage in an ice-box (mp 41°–42° C.). IR (KBr): 1700 cm$^{-1}$ (C=O). $^1$H NMR (CDCl$_3$): δ1.37, 1.39 (each 3H, s, 2×Me), 2.81 (1H, q, $J_{3,4}$=3.02 Hz, Ha-3), 2.83 (1H, t, $J_{2,3}$=2.74 Hz, Hb-3), 4.87 (1H, dt, $J_{3,4}$=3.02, $J_{4,5}$=6.04 Hz, H-4), 5.30 (1H, d, $J_{4,5}$=6.04 Hz, H-5), 6.88 (1H, t, $J_{2,3}$=2.47 Hz, H-2), 9.82 (1H, s, CHO). Anal. Calc'd for C$_9$H$_{12}$O$_3$: C, 64.27; H, 7.19. Found: C, 64.31; H, 7.16.

By following the same procedure, the following compounds are prepared:
1-Formylcyclopent-1-ene,
4,5-dihydroxycarbonate-1-formylcyclopent-1-ene,
4,5-ethylidenedioxy-1-formylcyclopent-1-ene,
4,5-benzylidenedioxy-1-formylcyclopent-1-ene,
1-formyl-4,5-(1-methoxyethylidenedioxy)cyclopent-1-ene,
1-formyl-4,5-(α-methoxybenzylidenedioxy)cyclopent-1-ene,
4,5-di-(tert-butyldimethylsilyloxy)-1-formylcyclopent-1-ene, and
4,5-dibenzyloxy-1-formylcyclopent-1-ene.

EXAMPLE 4

1-(Cylopent-1-enyl)ethanol: A solution of 1-formylcyclopent-1-ene (16.72 g, 0.174 mol) in dry THF (10 mL) is added over a period of 15 minutes into a mixture of MeMgI [prepared from MeI (37.62 g, 0.265 mol) and Mg turnings (7.53 g, 0.31 mol)] in absolute ether (100mL), and then allowed to stand at room temperature overnight. The mixture is poured into ice (300 g), and treated with 1N HCl vigorously stirring to dissolve the precipitates. The mixture is then extraced with ether (100×3 mL). The combined extracts are washed with H$_2$O, dried (Na$_2$SO$_4$), and evaporated in vacuo to dryness. 1-(Cylopent-1-enyl)ethanol (17.03 g, 89%) is obtained as a syrup by vacuum distillation, bp$_{17}$ 75°–7° C. $^1$H NMR (CDCl$_3$): δ1.28 (3H, d, J=6.32 Hz, Me), 1.69–2.04 (2H, m, 4-CH$_2$), 2.32 (4H, t, J=6.32 Hz, 2- and 5-CH$_2$), 6.45 (1H, q, J=6.32 Hz, C$\underline{H}$—OH), 5.56 (1H, brs, =CH—). Anal. Calc'd for C$_7$H$_{12}$O: C, 74.95; H, 10.78. Found: C, 74.86; H, 10.95.

In a similar manner, the following compounds are synthesized:
1-(4,5-Isopropylidenedioxy-cyclopent-1-enyl)ethanol,
1-(4,5-dihydroxycarbonate-cyclopent-1-enyl)ethanol,
1-(4,5-ethylidenedioxy-cyclopent-1-enyl)ethanol,
1-(4,5-benzylidenedioxy-cyclopent-1-enyl)ethanol,
1-[4,5-(1-methoxyethylidenedioxy)-cyclopent-1-enyl]ethanol,
1-[4,5-(α-methoxybenzylidenedioxy)-cyclopent-1-enyl]ethanol,
1-[4,5-di-(tert-butyldimethylsilyloxy)-cyclopent-1-enyl]ethanol, and
1-(4,5-dibenzyloxy-cyclopent-1-enyl)ethanol.

EXAMPLE 5

1-A cetylcyclopent-1-ene: A mixture of 1-(cyclopent-1-enyl)ethanol (6.5 g, 59 mmol) and MnO$_2$ (26.1 g) in CHCl$_3$ (150 mL) is heated at reflux for 3 days. After cooling the mixture is filtered through a pad of Celite and washed with CHCl$_3$. The combined filtrate and washings are evaporated in vacuo and the residue is vacuum distilled to yield 1-acetylcyclopent-1-ene, 5.01 g (77%), bp$_{17}$ 61°–63° C. (Lit.[15] bp$_{18}$ 65°–68° C). $^1$H NMR (CDCl$_3$): δ1.75–2.25 (2H, m, 4-CH$_2$), 2.32 (3H, s, Me), 2.56 (4H, t, J=6.86 Hz, 3- and 5-CH$_2$), 6.74 (1H, t, J=0.81 Hz, =CH—). Anal. Calc'd for C$_7$H$_{10}$O: C, 76.32; H, 9.15. Found: C, 76.09; H, 9.21.

By following the same procedure but using 1-(4,5-isopropylidene-dioxy-cyclopent-1-ene)ethanol as the starting material, the following compounds are prepared:
1-Acetyl-4,5-isopropylidenedioxy-cyclopent-1-ene,
1-acetoxy-4,5-dihydroxycarbonate-cyclopent-1-ene,
1-acetoxy-4,5-ethylidenedioxy-cyclopent-1-ene,
1-acetoxy-4,5-benzylidenedioxy-cyclopent-1-ene,
1-acetoxy-4,5-(1-methoxyethylidenedioxy)-cyclopent-1-ene,
1-acetoxy-4,5-(α-methoxybenzylidenedioxy)-cyclopent-1-ene,
1-acetoxy-4,5-di-(tert-butyldimethylsilyloxy)-cyclopent-1ene, and
1-acetoxy-4,5-dibenzyloxy-cyclopent-1-ene.

EXAMPLE 6

(4,5-Isopropylidenedioxy-cyclopent-1-enyl)ethene: A solution of 1-formyl-4,5-isopropylidenedioxy-cyclopent-1-ene (0.5 g, 2.7 mmol) in dry THF (2 mL) is added dropwise to a solution of triphenyl-phosphinemethylene (prepared from methyltripheneyl-phosphonioum bromide, 2.14 g, 6 mmol, and n-BuLi, 6 mmol) in dry THF (20 mL) at −78° C. The reaction mixture is allowed to warm to room temperature within 1 hour, quenched with saturated NH$_4$Cl aqueous solution, and extracted with EtOAC (20 mL×3). The combined extracts are washed with H$_2$O, dried (Na$_2$SO$_4$), and evaporated in vacuo to dryness. The residue was chromatographed over a silica gel column (n-pentane/ether, 10:1 v/v) to give (4,5-isopropylidenedioxy-cyclopet-1-enyl)ethene, 268 mg (54%) as a colorless liquid. $^1$H NMR (CDCl$_3$): δ1.34 (6H, s, 2×Me), 2.59 (2H, m, 2×H-3), 4.71–4.85 (1H, m, H-4), 5.11–5.24 (2H, m H-5, H-2'), 5.43 (1H, d, $J_{1',2}$=17.6 Hz, H-2'), 5.65– 5.71 (1H, m, H-2), 6.47 (1H, dd, $J_{1',2}$=10.7 Hz, H-1').

By following the same procedure, the following compounds are prepared:
(Cyclopent-1-enyl)ethene,
(4,5-dihydroxycarbonate-cyclopent-1-enyl)ethene,
(4,5-ethylidenedioxy-cyclopent-1-enyl)ethene,
(4,5-benzylidenedioxy-cyclopent-1-enyl)ethene,
[4,5-(1-methoxyethylidenedioxy)-cyclopent-1-enyl]ethene,
[4,5-(α-methoxybenzylidenedioxy)-cyclopent-1-enyl]ethene,
[4,5-di-(tert-butyldimemethylsilyloxy)-cyclopent-1-enyl]ethene, and
(4,5-dibenzyloxy-cyclopent-1-enyl)ethene.

EXAMPLE 7

1-Acetory-1-(4,5-isoproylidenedioxy-cyclopent-1-enyl)ethene: A solution of 1-acetyl-4,5-isopropylidenedioxy-cyclopent-1-ene (3.0 g, 16.5 m mol) in dry THF (16 mL) is slowly added to a mixture of LDA (freshly prepared from n-BuLi, 25 mmol, and diisopropylamine, 25 mmol) in dry THF (50 mL) at −78° C. After stirring for 5 minutes, acetic anhydride (5 g, 49.5 mmol) is added to the reaction mixture, which is continuously stirred for 10 minutes. The reaction is quenched with saturated NaHCO$_3$ aqueous solution and extracted with ether (100 mL×4). The combined extracts are washed with H$_2$O, dried (Na$_2$SO$_4$), and evaporated in vacuo to dryness to give crude 1-acetoxy-1-(4,5-isopropylidenedioxy-cyclopent-1-enly)ethene (3.25 g) as a syrup, which can be used directly in the next step without further purification. A small amount of the crude product can be purified by silica gel column chromatography (C₆H₅CH₃/EtOAC, 9:1 v/v) for ¹H NMR spectrometrical measurements. ¹H NMR (CDCl₃): δ1.37 and 1.38 (each 3H, s, 2×Me), 2.20 (3H, s, Ac), 2.57–2.66 (2H, m, 2×H-3), 4.71–4.86 (1H, m, H-4), 4.94 (1H, d, $J_{2',2}$=1.1 Hz, H-2'), 5.20 (1H, dd, $J_{4,5}$=5.8 Hz, $J_{5,2}$=0.8 Hz, H-5), 5.30 (1H, dd, $J_{5,2}$= 1.10 Hz, J=0.8 Hz, H-2'), 5.75 (1H, t, $J_{2,3}$=2.5 Hz, H-2).

By following the same procedure but using tert-butyldimethylsilyltrifluoromethanesulfonate instead of acetic anhydride, the following compounds are prepared:

1-Acetoxy-1-(cyclopent-1-enyl)ethene,
1-acetoxy-1-(4,5-isopropylidenedioxy-cyclopent-1-enly-)ethene,
1-acetoxy-1-(4,5-dihydroxycarbonate-cyclopent-1-enly-)ethene,
1-acetoxy-1-(4,5-ethylidenedioxy-cyclopent-1-enly)ethene,
1-acetoxy-1-(4,5-benzylidenedioxy-cyclopent-1-enly-)ethene,
1-acetoxy-1-[4,5-(1-methoxyethylidenedioxy)-cyclopent-1enly]ethene,
1-acetoxy-1-[4,5-(α-methoxybenzylidenedioxy)-cyclopent-1enly]ethene,
1-acetoxy-1-[4,5-di-(tert-butyldimethylsilyloxy)-cyclopent-1-enly]ethene,
1-acetoxy-1-(4,5-dibenzyloxy-cyclopent-1-enly)ethene,
1-tert-butyldimethylsilyloxy-1-(4,5-isopropylidenedioxy-cyclopent-1-enly)ethene,
1-tert-butyldimethylsilyloxy-1-(cyclopent-1-enly)ethene,
1-tert-butyldimethylsilyloxy-1-(4,5-isopropylidenedioxy-cyclopent-1-enly)ethene,
1-tert-butyldimethylsilyloxy-1-(4,5-dihydroxycarbonate-cyclopent-1-enly)ethene,
1-tert-butyldimethylsilyloxy-1-(4,5-ethylidenedioxy-cyclopent-1-enly)ethene,
1-tert-butyldimethylsilyloxy-1-(4,5-benzylidenedioxy-cyclopent-1-enly)ethene,
1-tert-butyldimethylsilyloxy-1-[4,5-(1-methoxyethylidenedioxy)-cyclopent-1-enly]ethene,
1-tert-butyldimethylsilyloxy-1-[4,5-(α-methoxybenzylidene-dioxy)-cyclopent-1-enly]ethene,
1-tert-butyldimethylsilyloxy-1-[4,5-di-(t-butyldimethylsilyloxy)-cyclopent-1-enly]ethene, and
1-tert-butyldimethylsilyloxy-1-(4,5-dibenzyloxy-cyclopent-1-enly]ethene.

EXAMPLE 8

1-(Cyclopent-1-enyl)-2-phenylthioethanol: To a solution of thioanisol (3.73 g, 30 mmol) in a mixture of dry THF (50mL) and HMPA (14 mL) is added dropwise a solution of tert-butyllithium in pentane (30 mmol) at −78° C. over a period of 10 minutes. The resulting yellow-orange mixture is stirred at ambient temperature for an additional 45 minutes. A solution of 1-formyl-cyclopent-1-ene (2.88 g, 30 mmol) in dry THF (10 mL) is then added slowly. After stirring for 5 minutes, the reaction mixture is quenched with saturated ammonium chloride (20 mL), and allowed to warm to room temperature. The mixture is diluted with H₂O (100 mL) and extracted with ethyl acetate (50 mL×3). The combined extracts are washed with H₂O, dried (Na₂SO₄) and evaporated in vacuo to dryness. The residue is chromatographed over a silica gel column (5×30 cm) using toluene/EtOAc (9:1) as the eluent. The desired product is obtained as a pale yellow syrup, 5.0 g (76%). ¹H NMR (CDCl₃): δ1.66–1.99 (2H, m, CH₂-4'), 2.16–2.38 (4H, m, CH₂-3' and CH₂-5'), 2.61 (1H, brs, OH), 2.98 (1H, dd, J=8.21 Hz, J=13.45 Hz, Ha-2), 3.23 (1H, dd, J=4.39 Hz, J=13.45 Hz, Hb-2), 4.33 (1H, dd, J=4.39, J=8.21 Hz, H-1), 5.67 (1H, brs, H-1'), 7.14–7.45 (5H, m, Ph). Anal. Calc'd for $C_{13}H_{16}OS$: C, 70.87; H, 7.32; S, 14.34. Found: C, 70.88; H, 7.83; S, 14.37.

By following the same procedure but using 1-formyl-3,4-isopropyl-idinedioxy-cyclopent-1-ene as the starting material, the following compounds are prepared:

1-(4,5-Isopropylidenedioxy-cyclopent-1-enyl)-2-phenylthioethanol,
1-(4,5-dihydroxycarbonate-cyclopent-1-enyl)-2-phenylthioethanol,
1-(4,5-ethylidenedioxy-cyclopent-1-enyl)-2-phenylthioethanol,
1-(4,5-benzylidenedioxy-cyclopent-1-enyl)-2-phenylthioethanol,
1-[4,5-(1-methoxyethylidenedioxy)-cyclopent-1-enyl]-2-phenylthioethanol,
1-[4,5-(α-methoxybenzylidenedioxy)-cyclopent-1-enyl]-2-phenylthioethanol,
1-[4,5-di-(t-butyldimethylsilyloxy)-cyclopent-1-enyl]-2-phenylthioethanol, and
1-(4,5-dibenzyloxy-cyclopent-1-enyl]-2-phenylthioethanol.

EXAMPLE 9

Cyclopent-1-enyl phenylthiomethyl ketone: DDQ (3.7 g, 16.3 mmol) is added to a solution of 1-(cyclopent-1-enyl)-2-phenylthio-ethanol (3.14 g, 14.3 mmol) in tert-butanol (50 mL). The mixture is stirred at room temperature for 4 hours and the solvent is removed by evaporation in vacuo. The residue is triturated with dichloromethane (100 mL) and filtered. The filtrate is evaporated in vacuo to dryness and the residue was chromatographed over a silica gel column (5×30 cm) using dichloromethane as the eluent. The product, cyclopent-1-enyl pheylthiomethyl ketone, 2.83 g (90%), slowly crystallized on storage in an ice-box, mp 33°–34° C. ¹H NMR (CDCl₃): δ1.73–2.08 (2H, m, CH₂-4), 2.46–2.64 (4H, m, CH₂-3 and CH₂-5), 3.95 (2H, s, CH₂-S), 6.79 (1H, brs, H-2), 7.17–7.45 (5H, m, Ph). Anal. Cacl'd for $C_{13}H_{14}SO$: 71.52; H, 6.46; S, 14.69. Found: C, 71.52; H, 6.32; S, 14.77.

By following the same procedure, the following compounds are prepared:

4,5-isopropylidenedioxy-cyclopent-1-enyl phenylthiomethyl ketone,
4,5-dihydroxycarbonate-cyclopent-1-enyl phenylthiomethyl ketone,
4,5-ethylidenedioxy-cyclopent-1-enyl phenylthiomethyl ketone,
4,5-benzylidenedioxy-cyclopent-1-enyl phenylthiomethyl ketone,
4,5-(1-methoxyethylidenedioxy)-cyclopent-1-enyl phenylthiomethylketone,
4,5-(α-methoxybenzylidenedioxy)-cyclopent-1-enyl phenylthiomethylketone,
4,5-di-(tert-butyldimethylsilyloxy)-cyclopent-1-enyl phenylthiomethyl ketone, and
4,5-dibenzyloxy-cyclopent-1-enyl phenylthiomethyl ketone.

EXAMPLE 10

S-[3-Phenylthio-2-hydroxy-2-(cyclopent-1-enyl)propyl]-N-methyl-S-phenylsulfoximine: To a mixture of S-methyl-N-methyl-S-phenyl-sulfoximine (2.04 g, 12 mmol) and triphenylmethane (5 mg) in dry THF (20mL) is added dropwise to a solution of n-butyllithium (1.6 mol) in hexane (7.5 mL, 12 mmol) at 0° C. A solution of phenylthio-methyl cyclopent-1-enyl ketone (2.18 g, 10mmol) in dry THF (10 mL) is then added slowly during a period of 10 minutes. After stirring at 0° C. for 30 minutes, the mixture is poured into a 5% ammonium chloride aqueous solution (50 mL) and extracted with dichloromethane (40 mL×3). The combined extracts are washed with $H_2O$, dried ($Na_2SO_4$), and evaporated in vacuo to dryness. The thin layer chromatography (TLC, $SiO_2$, toluene/EtOAc, 9:1 v/v) of the mixture showed that it contains a mixture of diastereomers in a syrup, 2.70 g (70%) (Rf=0.43 and 0.37), which are isolated by liquid chromatography ($SiO_2$, touene/EtOAc, 9:1 v/v) and used directly in the next step without further separation.

A small amount of the mixture of diastereomers can be separated by chromatography on a silica gel column (5×30 cm) using toluene/EtOAc (9:1 v/v) as the eluent. The compound with higher Rf value (0.43) is eluted first as a colorless syrup; $^1$HNMR ($CDCl_3$): δ1.54–2.32 (6H, m, $CH_2$-3, -4 and -5), 2.66 (3H, s, Me), 3.502 (2H, q, J=12.9 Hz, —$CH_2$—SON), 3.504 (2H, q, J=14.0 Hz, —$CH_2$—S—), 5.69 (1H, t, J= 1.93 Hz, H-2), 7.12–7.89 (10H, m, ArH). The compound with lower Rf value (0.37) is eluted later as a colorless syrup; $^1$H NMR ($CDCl_3$): δ1.79 (2H, q, J=6.86 Hz, $CH_2$-4), 2.16–2.32 (4H, m, $CH_2$-3 and -5), 2.58 (3H, s, Me), 3.13 (2H, q, J=12.9 Hz, —$CH_2$—SON), 3.52 (2H, q, $CH_2$-S), 5.87 (1H, t, J=1.93 Hz, H-2), 7.12–7.89 (10H, m, ArH).

By following the same procedure, the following compounds are prepared:

S-[3-phenylthio-2-hydroxy-2-(4,5-isopropylidenedioxy-cyclopent- 1-enyl)propyl]-N-methyl-S-phenylsulfoximin S-[3-phenylthio-2-hydroxy-2-(4,5-dihydroxycarbonate-cyclopent- 1-enyl)propyl]-N-methyl-S-phenylsulfoximine, S-[3-phenylthio-2-hydroxy-2-(4,5-ethylidenedioxy-cyclopent-1-enyl)propyl]-N-methyl-S-phenylsulfoximine, S-[3-phenylthio-2-hydroxy-2-(4,5-benzylidenedioxy-cyclopent-1-enyl)propyl]-N-methyl-S-phenylsulfoximine, S-[3-phenylthio-2-hydroxy-2-(4,5-(1-methoxyethylidene-dioxy-cyclopent- 1-enyl)propyl]-N-methyl-S-phenylsulfoximine, S-[3-phenylthio-2-hydroxy-2-(4,5-(α-methoxybenzylidene-dioxy)-cyclopent- 1-enyl)propyl]-N-methyl-S-phenylsulfoximine, S-[3-phenylthio-2-hydroxy-2-(4,5-di-(t-butyldimethylsilyloxy)-cyclopent- 1-enyl)propyl]-N-methyl-S-phenylsulfoximine, and S-[3-phenylthio-2-hydroxy-2-(4,5-dibenzyloxy-cyclopent-1-enyl)propyl]-N-methyl-S-phenylsulfoximine.

EXAMPLE 11

2-(Cyclopent-1-enyl)-3-phenylthio-prop-1-ene: To a solution of S-[1-phenylthio-2-hydroxy-2-(cyclopent-1-enyl)propyl]-N-methyl-S-phenylsulfoximine (1.05 g, 2.7 mmol) in a mixture of THF (20 mL), $H_2O$ (8 mL) and acetic acid (8 mL) is added freshly prepared Al/Hg (1.3 g) in an ice-bath. After stirring at 0° C. for 5 hours, the mixture is filtered through a pad of Celite and the Celite is washed with EtOH (10 mL). The filtrate is concentrated in vacuo to ca. 5 mL. The residue is diluted with $H_2O$ (100 mL) and extracted with pentane (40 mL×5). The combined extracts are dried ($Na_2SO_4$), and evaporated in vacuo to dryness. The residue is chromatographed over a silica gel column (2×40 cm) using pentane as the eluent. The product is obtained as a syrup, 486 mg (83%). $^1$H NMR ($CDCl_3$): δ1.73–2.08 (2H, m, $CH_2$-4), 2.49 (4H, t, J=6.72 Hz, $CH_2$-3 and -5), 3.78 (2H, s, $CH_2$—S), 5.01 (2H, d, J=6.86 Hz, $CH_2$=), 5.90 (1H, brs, CH=), 7.11–7.53 (5H, m, pH).

In a similar manner, the following compounds are synthesized:

2-(4,5-Isopropylidenedioxy-cyclopent-1-enyl)-3-phenylthio-prop-1-ene, 2-(4,5-dihydroxycarbonate-cyclopent-1-enyl)-3-phenylthio-prop-1-ene, 2-(4,5-ethylidenedioxy-cyclopent-1-enyl)-3-phenylthio-prop-1-ene, 2-(4,5-benzylidenedioxy-cyclopent-1-enyl)-3-phenylthio-prop-1-ene, 2-[4,5-(1-methyoxyethylidenedioxy)-cyclopent-1-enyl]-3-phenylthio-prop-1-ene, 2-[4,5-(α-methoxyethylidenedioxy)-cyclopent-1-enyl]-3-phenylthio-prop-1-ene, 2-[4,5-di-(t-butyldimethylsilyloxy)-cyclopent-1-enyl]-3-prop-1-ene, and 2(4,5-dibenzyloxy-cyclopent-1-enyl)-3-phenylthio-prop-1-ene.

EXAMPLE 12

4-Acetoxy-2,3-dihydro-2,3-isopropylidenedioxy-1H-cyclopent[a]-anthracene- 6,11-dione: A mixture of 1-acetoxy-1-(4,5-isopropylidenedioxy-cyclopent-1-eny)1-ethene (925 mg, 4.1 mmol) and naphthoquinone (1.50 g, 9.5 mmol) in toluene (20 mL) is refluxed for 6 hours, and then allowed to cool to room temperature. The mixture is filtered to remove dark blue precipitate deposits in the reaction mixture. The filtrate is evaporated in vacuo and the dark residue is crystallized from EtOH. The residue is crystallized from ethanol to give 4-acetoxy-2,3-dihydro-2,3-isopropylidenedioxy- 1H-cyclopent[a]anthracene-6,11-dione, 543 mg (37%), mp 197°–199° C. $^1$H NMR ($CDCl_3$): δ1.21 and 1.41 (each 3H, s, 2×Me), 2.41 (3H, s, Ac), 3.56 (1H, dd, $J_{1,1'}$=19.48 Hz, $J_{1,2}$=5.21 Hz, H-1), 3.91 (1H, d, $J_{1,1'}$=19.84 Hz, H-1'), 5.06 (1H, dt, $J_{2,3}$=1.10 Hz, $J_{2,3}$=5,76 Hz, H-2), 5.56 (1H, d, $J_{3,4}$=5.76 Hz, H-3), 7.73–8.32 (5H, m, At—H). Anal. Calc'd for $C_{22}H_{18}O_6$: C, 69.83; H, 4.79. Found: C, 69.80; H, 4.80.

In a similar manner, the following compounds are prepared by the Dieis-Alder reaction of various benzoquinones or naphthoquinones with the dienes:

4-Acetoxy-2,3-dihydro-2,3-isopropylidenedioxy-1H-benz[e]inden-6,9-dione, 4-acetoxy-2,3-dihydroxycarbonate-2,3-dihydro-7-methoxy-8-methyl-1H-benz[e]inden-6,9-dione, 4-acetoxy-2,3-ethylidenedioxy-2,3-dihydro-7,8-dimethoxy-1H-benz[e]inden-6,9-dione, 4-tert-butyldimethylsilyloxy-2,3-dihydro-2,3-isopropylidenedioxy-1H-benz[e]inden-6,9-dione, 4-tert-butyldimethylsilyloxy-2,3-dihydroxycarbonate-2,3-dihydro-1H-benz[e]inden-6,9-dione, 4-tert-butyldimethylsilyloxy-2,3-dihydro-2,3-ethylidene-dioxy- 7-methoxy-8-methyl-1H-benz[e]inden-6,9-dione, 2,3-dihydro-2,3-isopropylidenedioxy-4-phenylthiomethyl-1H-benz[e]inden-6,9-dione, 2,3-dihydro-2,3-isopropylidenedioxy-7-methoxy-8-methyl-4-phenylthiomethyl- 1H-benz[e]inden-6,9dione, 2,3-dihydro-2,3-dihydroxycarbonate-7,8-dimethoxy-4-phenylthio-methyl-1H-benz[e]inden-6,9-dione, 4-acetoxy-2,3-dihydro-2,3-dihydroxycarbonate-1H-cyclopent[a]-anthracene-6,11-dione, 7-acetoxy-2,3-dihydro-2,3-ethylidenedioxy-1H-cyclopent[a]anthracene-6,11-dione, 8-acetoxy-2,3-benzylidenedioxy-2,3-dihydro-1H-cyclopent[a]anthracene-6,11-dione, 9-acetoxy-2,3-dihydro-2,3-isopropylidenedioxy-1H-cyclopent[a]-anthracene-6,11-dione,
4-tert-butyldimethylsilyloxy-2,3-dihydro-2,3-isopropylidenedioxy- 1H-cyclopent[a]anthracene-6,11-dione,
4-tert-butyldimethylsilyloxy-2,3-dihydroxycarbonate-2,3-dihydro- 7-methoxy-1H-cyclopent[a]anthracene-6,11-dione,
4-tert-butyldimethylsilyoxy-2,3-dihydro-2,3-ethylidenedioxy-8-methoxy-1H-cyclopent[a]anthracene-6,11-dione,
2,3-dihydro-2,3-isopropylidenedioxy-4-phenylthiomethyl-1H-cyclopent[a]anthracene-6,11-dione,
2,3-dihydro-2,3-dihydroxycarbonate-4-phenylthiomethyl-1H-cyclopent[a]anthracene-6,11-dione,
2,3-ethylidenedioxy-2,3-dihydro-4-phenylthiomethyl-1H-cyclopent[a]anthracene-6,11-dione, and
2,3-benzylidenedioxy-2,3-dihydro-4-phenylthiomethyl-1H-cyclopent[a]anthracene-6,11-dione.

EXAMPLE 13

2,3-dihydro-4-hydroxy-2,3-isopropylidene-diox -1H-cyclopent[a]anthracene-, 6,11-dione:

Method 1: A mixture of 1-acetoxy-1-(4,5-isopropylidenedioxy-cyclopent- 1-enyl)ethene (672 mg, 3 mmol) and naphthoquinone (1.42 g, 9 mmol) in toluene (12 mL) is heated at reflux for 20 hours. After cooling, the precipitated product is collected by filtration and recrystallized from ether to give 2,3-dihydro-4-hydroxy-2,3-isopropylidenedioxy- 1H-cyclopent[a]anthracene-6,11-dione, 957 mg (95%), mp 272°–274° C. (dec.). $^1$H NMR (DMSO-$d_6$): δ1.20, 1.35 (each 3H, s, 2×Me), 3.48 (2H, d, $J_{1,2}$=3.57 Hz, 1-CH$_2$), 5.02 (1H, m, $J_{1,2}$=3.57 Hz, $J_{2,3}$=6.31 Hz, H-2), 5.54 (1H, d, $J_{2,3}$=6.31 Hz, H-3), 7.51 (1H, s, H-5), 7.79–8.16 (4H, m, Ar—H), 11.18 (1H, br, exchangeable, OH). Anal. Cacl'd for $C_{20}H_{16}O_5$: C, 71.42; H, 4.80. Found: C, 71.27; H, 4.87.

Method 2: A mixture of 4-acetoxy-2,3-dihydro-2,3-isopropylidenedioxy- 1H-cyclopent[a]anthracene-6,11-dione (1.16 g, 3.07 m mol) in MeOH (20 mL) containing H$_2$O (6 mL) and Et$_3$N (3 mL) is heated at 50° C. for 1.5 hours. The solvent is removed in vacuo, and the residue is coevaporated several times with MeOH. The resulting residue is crystallized from EtOH to yield 2,3-dihydro-4-hydroxy-2,3-isopropylidenedioxy-1H-cyclopent[a]anthracene-6,11-dione, 951 mg (92%). This sample is identical to the constituent prepared by Method 1.

Method 3: To a solution of 4-tert-butyloxy-2,3-dihydro-2,3-isopropylidenedioxy- 1H-cyclopent [a]anthracene-6,11-dione (137 mg, 0.3 mmol) dissolved in THF/H$_2$O (6 mL, 4:1 v/v) is added tetrabutylammonium fluoride (100 mg). The mixture is stirred at room temperature for 15 minutes, diluted with CHCl$_3$ (100 mL), and then washed successively with 10% NH$_4$Cl aqueous solution (15 mL) and H$_2$O (20 mL×3). The organic layer is dried (NaSO$_4$), evaporated in vacuo to dryness, and the residue is crystallized from ether to afford 2,3-dihydro- 4-hydroxy-2,3-isopropylidenedioxy-1H-cyclopent[a]anthracene- 6,11-dione 92 mg, (90%). This sample is identical to the constituent prepared by Method 1.

By following the same procedure, the following compounds are prepared:
2,3-dihydro-4-hydroxy-2,3-isopropylidenedioxy-1H-benz[e]inden-6,9-dione,
2,3-dihydro-4-hydroxy-2,3-isopropylidenedioxy-7-methoxy-8-methyl-1H-benz[e]inden-6,9-dione,
2,3-dihydro-7,8-dimethoxy-4-hydroxy-2,3-isopropylidenedioxy-1H-benz[e]inden-6,9-dione,
2,3-dihydro-2,3-dihydroxycarbonate-4-hydroxy-1H-benz[e]inden-6,9-dione,
2,3-dihydro-2,3-dihydroxycarbonate-4-hydroxy-7-methoxy-8-methyl-1H-benz[e]inden-6,9-dione,
2,3-dihydro-2,3-ethylidenedioxy-4-hydroxy-7-methoxy-8-methyl-1H-benz[e]inden-6,9-dione,
2,3-dihydro-7-hydroxy-2,3-isopropylidenedioxy-1H-cyclopent[a]anthracene-6,11-dione,
2,3-dihydro-8-hydroxy-2,3-isopropylidenedioxy-1H-cyclopent[a]-anthracene-6,11-dione,
2,3-dihydro-9-hydroxy-2,3-isopropylidenedioxy-1H-cyclopent[a]-anthracene-6,11-dione,
2,3-dihydro-10-hydroxy-2,3-isopropylidenedioxy-1H-cyclopent[a]-anthracene-6,11-dione,
2,3-dihydro-2,3-dihydroxycarbonate-4-hydroxy-1H-cyclopent[a]-anthracene-6,11-dione,
2,3-dihydro-2,3-ethylidenedioxy-7-hydroxy-1H-cyclopent[a]anthracene-6,11-dione,
2,3-benzylidenedioxy-2,3-dihydro-8-hydroxy-1H-cyclopent[a]anthracene-6,11-dione, and
2, 3-dihydro-9-hydroxy-2,3-isopropylidenedioxy-1H-cyclopent[a]-anthracene-6,11-dione.

EXAMPLE 14

4-[2-bis(2-chloroethyl)amino]ethoxy-2,3-dihydro-2,3-isopropylidenedioxy- 1H-cyclopent[a]anthracene-6,11-dione: A mixture of 2,3-dihydro-4-hydroxy-2,3-isopropylidene-dioxy-1H-cyclopent[a]anthracene-6,11-dione (470 mg, 1.4 mmol), tris(2-chloroethyl)amine hydrochloride (720 mg, 3.0 mmol), and K$_2$CO$_3$ (4.0 g) in acetone (20 mL) is heated at reflux for 5 hours (the deep purple color disappears at this time). The mixture is filtered and washed with CHCl$_3$. The combined filtrate and washings are evaporated in vacuo to dryness. The residue is dissolved in CHCl$_3$ (80 mL), washed with H$_2$O, dried (Na$_2$SO$_4$), and evaporated to dryness. The residue is chromatographed over a silica gel column (2×30 cm) using toluene/EtOAc (20:1 v/v) as the eluent to give 4-[2-(N,N-bis(2-chloroethyl))amino]ethoxy-2,3-dihydro-1H-cyclopent[a]anthracene- 6,11-dione, 306 mg (43%), mp 156°–158° C. (Et$_2$O). $^1$H NMR (CDCl$_1$): δ1.31 and 1.44 (each 3H, s, 2×Me), 3.01– 3.24 (6H, m, 2×Cl—CH$_2$—CH$_2$—, 1×N—CH$_2$—), 3.58 (2H, d, $J_{1,2}$= 3.01 Hz, 1-CH$_2$), 3.53–3.73 (4H, m, 2×Cl—CH$_2$), 4.24–4.40 (2H, m 2×O—CH$_2$—), 5.08 (1H, dt, $J_{2,3}$=6.31 Hz, $J_{1,2}$=3.01 Hz, H-2), 5.61 (1H, d, $J_{2,3}$=6.31 Hz, H-3), 7.67 (1H, s, H- 5), 7.70–8.29 (4H, m, Ar—H). Anal. Calc'd for $C_{26}H_{27}Cl_2NO_5$: C, 61.91; H, 5.40; Cl, 14.06; N, 2.78. Found: C, 62.03; H, 5.60; Cl, 14.11; N, 2.70.

By following the same procedure, the following compounds are prepared:
4-[2-Bis(2-chloroethyl)amino]ethoxy-2,3-dihydro-2,3-isopropylidenedioxy- 1H-benz[e]inden-6,9-dione,
4-[2-bis(2-chloroethyl)amino]ethoxy-2,3-dihydro-2,3-isopropylidene-dioxy- 7-methoxy-8-methyl-1H-benz[e]inden-6,9-dione,
4-[2-bis(2-chloroethyl)amino]ethoxy-2,3-dihydro-7,8-dimethoxy- 2,3-isopropylidene-dioxy-1H-benz[e]inden-6,9dione,
4-[2-bis(2-chloroethyl)amino]ethoxy-2,3-dihydro-2,3-dihydroxycarbonate- 1H-benz[e]inden-6,9-dione,
4-[2-bis(2-hydroxyethyl)amino]ethoxy-2,3-dihydroxycarbonate-2,3-dihydro-7-methoxy-8-methyl-1H-benz[e]inden-6,9-dione,
4-[2-bis(2-hydroxyethyl)amino]ethoxy-2,3-dihydro-2,3-ethylidenedioxy- 7-methoxy-8-methyl-1H-benz[e]inden-6,9-dione, 7-[2-bis(2-chloroethyl)amino]ethoxy-2,3-dihydro-2,3-isopropylidenedioxy- 1H-cyclopent[a]anthracene-6,11-dione, 8-[2-bis(2-chloroethyl)amino]ethoxy-2,3-dihydro-2,3-isopropylidenedioxy- 1H-cyclopent[a]anthracene-6,11-dione, 9-[2-bis(2-chloroethyl)amino]ethoxy-2,3-dihydro-2,3-isopropylidenedioxy- 1H-cyclopent[a]anthracene-6,11-dione, 10-[2-bis(2-chloroethyl)amino]ethoxy-2,3-dihydro-2,3-isopropylidenedioxy- 1H-cyclopent[a]anthracene-6,11-dione, 4-[2-bis(2-chloroethyl)amino]ethoxy-2,3-dihydro-2,3-dihydroxycarbonate- 1H-cyclopent[a]anthracene-6,11-dione, 7-[2-bis (2-hydroxyethyl) amino]ethoxy-2,3-dihydro-2,3-ethylidenedioxy- 1H-cyclopent[a]anthracene-6,11-dione, and 2,3-benzylidenedioxy-8-[2-bis(2-hydroxyethyl)amino] ethoxy-2,3-dihydro-1H-cyclopent[a]anthracene-6,11-dione.

EXAMPLE 15

2,3-dihydro-4-bromomethyl-1H-cyclopent[a]anthracene-6,11-dione: A mixture of 2,3-dihydro-4-phenylthiomethyl-1H-cyclopent[a]-anthracene- 6,11-dione (350 mg, 0.95 mmol) and cyanogen bromide solution (5.0M) in acetonitrile (8 mL, 4 mmol) is heated at reflux for 4.5 hours under nitrogen. After cooling, the mixture is washed with $H_2O$ (20 mL×3), dried ($Na_2SO_4$) and evaporated in vacuo to dryness. The residue is then treated with boiling ethyl ether for 10 minutes and then stored in the refrigerator overnight. The product, 2,3-dihydro-4-bromomethyl-1H-cyclopent[a]-anthracene- 6,11-dione (208 mg, 61%), is obtained after filtration and dried, mp 225°–230° C. The compound is used directly in the next step without further purification. $^1H$ NMR ($CDCl_3$): δ2.22 (2H, dt, J=7.14 Hz, J=7.69 Hz, $CH_2$-2), 3.06 (2H, t, J=7.14 Hz, $CH_2$-3), 3.53 (2H, t, J=7.69 Hz, $CH_2$-1), 4.54 (2H, s, $CH_2$—S), 7.22–8.37 (5H, m, Ar—H).

By following the same procedure, the following compounds are prepared:

4-Bromomethyl-2,3-dihydro-2,3-isopropylidenedioxy-1H-benz[e]inden-6,9-dione, 4-bromomethyl-2,3-dihydro-2,3-isopropylidenedioxy-7-methoxy-8-methyl- 1H-benz[e]inden-6,9-dione, 4-bromomethyl-2,3-dihydro-7,8-dimethoxy-2,3isopropylidenedioxy-1H-benz[e]inden-6,9-dione, 4-bromomethyl-2,3-dihydro-2,3-dihydroxycarbonate-1H-benz[e]inden-6,9-dione, 4-bromomethyl-2,3-dihydro-2,3-dihydroxycarbonate-7-methoxy-8-methyl- 1H-benz[e]inden-6,9-dione, 4-bromomethyl-2,3-dihydro-2,3-ethylidenedioxy-7-methoxy-8-methyl- 1H-benz[e]inden-6,9-dione, 4-bromomethyl-2,3-dihydro-2,3-isopropylidenedioxy-1H-cyclopent[a]-anthracene-6,11-dione, 4-bromomethyl-2,3-dihydro-2,3-benzylidenedioxy-1H-cyclopent[a]-anthracene-6,11-dione, 4-bromomethyl-2,3-dihydro-2,3-isopropylidenedioxy-8-methoxy-1H-cyclopent[a]anthracene-6,11-dione, 4-bromomethyl-2,3-dihydro-2,3-isopropylidenedioxy-9-methoxy-1H-cyclopent[a]anthracene-6,11-dione, 4-bromomethyl-2,3-dihydroxycarbonate-2,3-dihydro-1H-cyclopent[a]anthracene-6,11-dione, 4-bromomethyl-2,3-dihydro-2,3-ethylidenedioxy-1H-cyclopent[a]anthracene-6,11-dione, and 2,3-benzylidenedioxy-4-bromomethyl-2,3-dihydro-1H-cyclopent[a]anthracene-6,11-dione.

EXAMPLE 16

4-acetoxymethyl-2,3-dihydro-1H-cyclopent[a]anthracene-6,11-dione: To a solution of 2,3-dihydro-4-bromomethyl-1H-cyclopent[a]-anthracene- 6,11-dione (173 mg, 0.51 mmol) in dimethylformamide (10 ml) is added anhydrous potassium acetate (200 mg) at 0° C. and stirred for 2.5 hours. The mixture is diluted with dichloromethane (50mL), washed with $H_2O$, dried ($Na_2SO_4$), and evaporated in vacuo to dryness. The residue is chromatographed on a silica gel column (2×30 cm) using toluene/ethyl acetate (9:1 v/v) as the eluent. The main fraction is collected, evaporated, and the solid residue is recrystallized from EtOH to afford 4-acetoxymethyl- 2,3-dihydro-1H-cyclopent[a]anthracene-6,11dione, 81 mg (50%), mp 160°–161° C. $^1H$ NMR ($CDCl_3$): δ2.18 (3H, s, Ac), 2.24 (2H, t, J=7.6 Hz, $CH_2$-2), 2.98 (2H, q, J=7.6 Hz, $CH_2$-3), 3.53 (2H, t, J=7.6 Hz, $CH_2$-1), 5.20 (2H, S, $CH_2$—OAc), 7.76–8.30 (5H, m, Ar—H). The product is used directly in the next step without further purification.

By following the same procedure, the following compounds are prepared:

4-Acetoxymethyl-2,3-dihydro-2,3-isopropylidenedioxy-1H-benz[e]inden-6,9-dione, 4-acetoxymethyl-2,3-dihydro-2,3-isopropylidenedioxy-7-methoxy-8-methyl-1H-benz[e]inden- 6,9-dione, 4-acetoxymethyl-2,3-dihydro-7,8-dimethoxy-2,3-isopropylidenedioxy-1H-benz[e]inden-6,9-dione, 4-acetoxymethyl-2,3-dihydro-2,3-dihydroxycarbonate-1H-benz[e]inden-6,9-dione, 4-acetoxymethyl-2,3-dihydro-2,3-dihydroxycarbonate-7-methoxy-8-methyl-1H-benz[e]inden- 6,9-dione, 4-acetoxymethyl-2,3-dihydro-2,3-ethylidenedioxy-7-methoxy-8-methyl-1H-benz[e]inden-6,9-dione, 4-acetoxymethyl-2,3-dihydro-2,3-isopropylidenedioxy-1H-cyclopent[a]-anthracene-6,11-dione, 4-acetoxymethyl-2,3-benzylidenedioxy-2,3-dihydro-1H-cyclopent[a]-anthracene-6,11-dione, 4-acetoxymethyl-2,3-dihydro-2,3-isopropylidenedioxy-8-methoxy-1H-cyclopent[a]anthracene-6,11-dione, 4-acetoxymethyl-2,3-dihydro-2,3-isopropylidenedioxy-9-methoxy-1H-cyclopent[a]anthracene-6,11-dione, 4-acetoxymethyl-2,3-dihydro-2,3-dihydroxycarbonate-1H-cyclopent[a]-anthracene-6,11-dione, 4-acetoxymethyl-2,3-dihydro-2,3-ethylidenedioxy-1H-cyclopent[a]-anthracene-6,11-dione, and 4-acetoxymethyl-2,3-benzylidenedioxy-2,3-dihydro-1H-cyclopent[a]-anthracene-6,11-dione. EXAMPLE 17

2,3-Dihydro-4-hydroxymethyl-1H-cyclopent[a]anthracene-6,11dione: A mixture of 2,3-dihydro-4-acetoxymethyl-1H-cyclopent[a]anthracene-6,11-dione (74 mg, 0.23 mmol) in MeOH (12 mL) containing $H_2O$ (3mL) and triethylamine (2mL) is heated at 55° C. for 3 hours. The mixture is evaporated in vacuo, and the residue is coevaporated twice with EtOH (10 mL) to dryness. The residue is recrystallized from $CHCl_3$ to give2,3-dihydro-4-hydroxymethyl-1H-cyclopent[a]anthracene-6,11-dione, 48 mg (75%), mp 191°–192° C. $^1H$ NMR (DMSO-$d_6$): δ2.14 (2H, q, J=7.6 Hz, $CH_2$-2), 2.88 (2H, t, J=7.6 Hz, $CH_2$-3), 3.40 (2H, t, J=7.6 Hz, $CH_2$-1), 4.61 (2H, d, J=5.5 Hz, $CH_2$—OH), 5.53 (1H, t, J=5.5 Hz, OH), 7.90–8.18 (5H, m, Ar—H). Anal. Calc'd for $C_{18}H_{14}O_3$: C, 77.68; H, 5.07. Found: C, 77.70; H, 5.06.

By following the same procedure, the following compounds are prepared:

2,3-Dihydro-4-hydroxymethyl-2,3-isopropylidenedioxy-1H-benz[e]inden-6,9-dione,
2,3-dihydro-4-hydroxymethyl-2,3-isopropylidenedioxy-7-methoxy-8-methyl-1H-benz[e]inden- 6,9-dione,
2,3-dihydro-7,8-dimethoxy-4-hydroxymethyl-2,3-isopropylidenedioxy-1H-benz[e]inden-6,9-dione,
2,3-dihydro-2,3-dihydroxycarbonate-4-hydroxymethyl-1H-benz[e]inden-6,9-dione,
2,3-dihydro-2,3-dihydroxycarbonate-4-hydroxymethyl-7-methoxy-8-methyl-1H-benz[e]inden- 6,9-dione,
2,3-dihydro-2,3-ethylidenedioxy-4-hydroxymethyl-7-methoxy-8-methyl-1H-benz[e]inden-6,9-dione,
2,3-dihydro-4-hydroxymethyl-2,3-isopropylidenedioxy-1H-cyclopent[a]anthracene-6,11-dione,
2,3-benzylidenedioxy-2,3-dihydro-4-hydroxymethyl-1H-cyclopent[a]anthracene-6,11-dione,
2,3-dihydro-4-hydroxymethyl-2,3-isopropylidenedioxy-8-methoxy- 1H-cyclopent[a]anthracene-6,11-dione,
2,3-dihydro-4-hydroxymethyl-2,3-isoporpylidenedioxy-9-methoxy- 1H-cyclopent[a]anthracene-6,11-dione,
2,3-dihydroxycarbonate-2,3-dihydro-4-hydroxymethyl-1H-cyclopent[a]anthracene-6,11-dione,
2,3-dihydro-2,3-ethylidenedioxy-4-hydroxymethyl-1H-cyclopent[a]anthracene-6,11-dione, and
2,3-benzylidenedioxy-2,3-dihydro-4-hydroxymethyl-1H-cyclopent[a]anthracene-6,11-dione.

EXAMPLE 18

2,3-Dihydro-4-hydroxymethyl-1H-cyclopent[a]anthracene-6,11-dione N-methyl carbamate A mixture of 2,3-dihydro-4-acetoxy- 1H-cyclopent[a]anthracene-6,11-dione (35 mg, 0.13 mmol1) and methylisocyanate (2 mL) in acetone (10 mL) is heated at reflux for 24 hours. After cooling in an ice-bath, the yellow precipitated product, 2,3-dihydro-4-hydroxymethyl-1H-cyclopent[a]anthracene-6,11-dione N-methylcarbamate (39 mg, 90%), is obtained by filtration and dried, mp 232°–233° C. $^1$H NMR (CDCl$_3$): δ2.14 (2H, q, J=7.5 Hz, CH$_2$-2), 2.86 (3H, d, J=4.7 Hz, N-Me), 2.97 (2H, t, J=7.5 Hz, CH$_2$-3), 3.52 (2H, t, J=7.5 Hz, CH$_2$-1), 4.85 (2H, brs, NH), 5.20 (2H, s, CH$_2$-O), 7.90–8.18 (5H, m, Ar—H). Anal. Calc'd for C$_{20}$H$_{17}$NO$_4$: C, 71.63; H, 5.14; N, 4.18. Found: C, 71.66; H, 5.17; N, 4.26.

By following the same procedure, the following compounds are prepared:
2,3-Dihydro-4-hydroxymethyl-2,3-isopropylidenedioxy-1H-benz[e]inden-6,9-dione carbamate,
2,3-dihydro-4-hydroxymethyl-2,3-isopropylidenedioxy-1H-benz[e]inden-6,9-dione N-methylcarbamate,
2,3-dihydro-4-hydroxymethyl-2,3-isopropylidenedioxy-7-methoxy- 8-methyl-1H-benz[e]inden-6,9-dione carbamate,
2,3-dihydro-4-hydroxymethyl-2,3-isopropylidenedioxy-7-methoxy- 8-methyl-1H-benz[e]inden-6,9-dione N-methylcarbamate,
2,3-dihydro-7,8-dimethoxy-4-hydroxymethyl-2,3-isopropylidenedioxy- 1H-benz[e]inden-6,9-dione carbamate,
2,3-dihydro-2,3-dihydroxycarbonate-4-hydroxymethyl-1H-benz[e]inden-6,9-dione N-methylcarbamate,
2,3-dihydro-2,3-dihydroxycarbonate-4-hydroxymethyl-7-methoxy-8-methyl-1H-benz[e]inden-6,9-dione carbamate,
2,3-dihydro-2,3-ethylidenedioxy-4-hydroxymethyl-7-methoxy-8-methyl- 1H-benz[e]inden-6,9-dione N-methylcarbamate,
2,3-dihydro-4-hydroxymethyl-2,3-isopropylidenedioxy-1H-cyclopent[a]anthracene- 6,11-dione carbamate,
2,3-dihydro-4-hydroxymethyl-2,3-isopropylidenedioxy-1H-cyclopent[a]anthracene- 6,11-N-methylcarbamate,
2,3-benzylidenedioxy-2,3-dihydro-4-hydroxymethyl-1H-cyclopent[a]-anthracene- 6,11-dione N-methylcarbamate,
2,3-dihydro-4-hydroxymethyl-2,3-isopropylidenedioxy-8-methoxy- 1H-cyclopent[a]anthracene-6,11-dione carbamate,
2,3-dihydro-4-hydroxymethyl-2,3-isopropylidenedioxy-9-methoxy- 1H-cyclopent[a]anthracene-6,11-dione carbamate,
2,3-dihydro-2,3-dihydroxycarbonate-4-hydroxymethyl-1H-cyclopent[a]anthracene- 6,11-dione carbamate,
2,3-dihydro-2,3-ethylidenedioxy-4-hydroxymethyl-1H-cyclopent[a]-anthracene- 6,11-dione N-methylcarbamate, and
2,3-benzylidenedioxy-2,3-dihydro-4-hydroxymethyl-1H-cyclopent[a]anthracene- 6,11-dione carbamate.

EXAMPLE 19

4-[2-Bis(2-chloroethyl)amino]ethoxy-2,3-dihydro-ccis-2,3-dihydroxy- 1H-cyclopent[a]anthracene-6,11-dione: 4-[2-N,N-Bis(2-cloro-ethyl)amino] ethoxy-2,3-dihydro-2,3-isopropylidenedioxy-1H-cyclopent[a]anthracene-6,11-dione (460 mg, 0.91mmol) is added to 80% trifluoroacetic acid (10 mL) in an ice-bath, and stirred for 1 hour. The reaction mixture is then diluted with ice-water (100 mL) and the precipitated product is collected by filtration and recrystallized from EtOH to give 4-[2-bis(2-chloroethyl)amino]ethoxy- 2,3-dihydro-cis-2,3-dihydroxy-1H-cyclopent[a]anthracene- 6,11-dione, 341 mg (81%), mp 130°–133° C. (EtOAc/Et$_2$O). $^1$H NMR (CDCl$_3$): δ2.95–3.19 (6H, m, 3×N—CH$_2$—), 3.50–3.66 (6H, m, 2×H-1, 2×Cl—CH$_2$—), 4.31 (2H, t, J=5.2 Hz, O—CH$_2$—), 4.60 (1H, q, J$_{1,2}$=J$_{1',2}$= J$_{2,3}$=5.21 Hz, H-2), 5.25 (1H, d, J$_{2,3}$=5.21 Hz, H-3), 7.67 (1H, s, H-5), 7.70–8.28 (4H, m, Ar—H). Anal. Calc'd for C$_{23}$H$_{23}$Cl$_2$NO$_5$: C, 59.49; H, 4.99; Cl, 15.27; N, 3.02. Found: C, 59.82; H, 5.25; Cl, 14.94; N, 3.01.

By following the same procedure, the following compounds are prepared:
4-[2-Bis(2-chloroethyl)amino]ethoxy-2,3-dihydro-2,3-dihydroxy- 1H-benz[e]inden-6,9-dione,
4-[2-bis(2-chloroethyl)amino]ethoxy-2,3-dihydro-2,3-dihydroxy- 7-methoxy-8-methyl-1H-benz[e]inden-6,9-dione,
4-[2-bis(2-chloroethyl)amino]ethoxy-2,3-dihydro-2,3-dihydroxy- 7,8-dimethoxy-1H-benz[e]inden-6,9-dione,
4-[2-bis(2-hydroxyethyl)amino]ethoxy-2,3-dihydro-2,3-dihydroxy-carbonate- 7-methoxy-8-methyl-1H-benz[e]inden 6,9-dione,
7-[2-bis(2-chloroethyl)amino]ethoxy-2,3-dihydro-2,3-dihydroxy- 1H-cyclopent[a]anthracene,6,11-dione,
8-[2-bis(2-chloroethyl)amino]ethoxy-2,3-dihydro-2,3-dihydroxy- 1H-cyclopent[a]anthracene,6,11-dione,
-[2-bis(2-chloroethyl)amino]ethoxy-2,3-dihydro-2,3-dihydroxy- 1H-cyclopent[a]anthracene,6,11-dione,
10-[2-bis(2-chloroethyl)amino]ethoxy-2,3-dihydro-2,3-dihydroxy- 1H-cyclopent[a]anthracene,6,11-dione,
7-[2-bis(2-hydroxyethyl)amino]ethoxy-2,3-dihydro-2,3-dihydroxy- 1H-cyclopent[a]anthracene,6,11-dione,
8-[2-bis(2-hydroxyethyl)amino]ethoxy-2,3-dihydro-2,3-dihydroxy- 1H-cyclopent[a]anthracene,6,11-dione,
2,3-dihydro-2,3-dihydroxy-4-hydroxymethyl-1H-benz[e]inden 6,9-dione carbamate,
2,3-dihydro-2,3-dihydroxy-4-hydroxymethyl-1H-benz[e]inden 6,9-dione N-methylcarbamate,
2,3-dihydro-2,3-dihydroxy-4-hydroxymethyl-7-methoxy-8-methyl- 1H-benz[e]inden-6,9-dione carbamate, 2,3-dihydro-2,3-dihydroxy-4-hydroxymethyl-7-methoxy-8-methyl- 1H-benz[e]inden-6,9-dione N-methylcarbamate,
2,3-dihydro-2,3-dihydroxy-4-hydroxymethyl-7,8-dimethoxy-1H-benz[e]inden- 6,9-dione carbamate,
2,3-dihydro-2,3-dihydroxy-4-hydroxymethyl-1H-cyclopent [a]anthracene- 6,11-dione carbamate,
2,3-dihydro-2,3-dihydroxy-4-hydroxymethyl-1H-cyclopent [a]anthracene- 6,11-dione N-methylcarbamate,
2,3-dihydro-2,3-dihydroxy-4-hydroxymethyl-8-methoxy-1H-cyclopent[a]anthracene- 6,11-dione carbamate, and
2,3-dihydro-2,3-dihydroxy-4-hydroxymethyl-9-methoxy-1H-cyclopent[a]anthracene- 6,11-dione N-methylcarbamate.

EXAMPLE 20

2,3-Dihydro-2,3-cis-di-mesyloxy-1H-cyclopent[a]anthracene-6,11-dione: A mixture of 4-[2-bis(2-hydroxyethyl)amino]ethoxy- 2,3-dihydro-cis-2,3-dihydroxy-1H-cyclopent[a]anthracene- 6,11-dione (860 mg, 3.07 mmol) and methanesulfonyl chloride (1.41 g, 12.3 mmol) in pyridine (10mL) is stirred in an ice-bath. After stirring for 1 hour, the reaction mixture is poured into ice-water (100 mL), and the precipitated product is collected by filtration. The filtrate is extrated with CHCl$_3$ (50 mL× 3), washed with H$_2$O, dried (Na$_2$SO$_4$), and evaporated to dryness. The solid residue is combined with the solid obtained previously, and recrystalized from acetone to give 2,3-dihydro-2,3-cis-di-mesyloxy-1H-cyclopent[a]anthracene 6,11-dione, 1.17 g (99%), mp 190°–191° C. (dec.). $^1$H NMR (DMSO-d$_6$): δ3.32 and 3.44 (each 3H, s, 2×Me), 3.81 (2H, d, J$_{1,2}$=4.39 Hz, 1-CH$_2$), 5.63 (1H, q, J$_{1,2}$=4.39 Hz J$_{2,3}$=4.94 Hz, H-2), 6.33 (1H, d, J$_{2,3}$=4.94 Hz, H-2), 6.33 (1H, d, J$_{2,3}$=4.94 Hz, H-3), 7.96 (1H, d, J$_{4,5}$=7.79 Hz, H-4), 8.24 (1H, d, J$_{4,5}$=7.79 Hz, H-5), 7.87–8.32 (4H, m, Ar—H). Anal Calc'd for C$_{19}$H$_{16}$O$_8$S$_2$: C, 52.28; H, 3.70; S, 14.69. found: C, 52.03; H, 3.91; S, 14.42.

By following the same procedure, the following compounds are prepared:
4-[2-Bis(2-chloroethyl)amino]ethoxy-2,3-dihydro-2,3-dimesyloxy- 1H-benz[e]inden-6,9-dione,
4-[2-bis(2-hydroxyethyl)amino]ethoxy-2,3-dihydro-2,3-dimesyloxy- 1H-benz[e]inden-6,9-dione,
4-[2-bis(2-chloroethyl)amino]ethoxy-2,3-dihydro-2,3-dimesyloxy- 7-methoxy-8-methyl-1H-benz[e]inden-6,9-dione,
4-[2-bis(2-chloroethyl)amino]ethoxy-2,3-dihydro-2,3-dimesyloxy- 7,8-dimethoxy-1H-benz[e]inden-6,9-dione,
2,3-dihydro-2,3-dimesyloxy-1H-cyclopent[a]anthracene-6,11dione,
4-[2-bis(2-hydroxyethyl)amino]ethoxy-2,3-dihydro-2,3-dimesyloxy- 8-methoxy-1H-cyclopent[a]anthracene-6,11-dione,
4-[2-bis(2-chloroethyl)amino]ethoxy-2,3-dihydro-2,3-dimesyloxy- 8-methoxy-1H-cyclopent[a]anthracene-6,11-dione,
7-[2-bis(2-chloroethyl)amino]ethoxy-2,3-dihydro-2,3-dimesyloxy- 1H-cyclopent[a]anthracene-6,11-dione,
8-[2-bis(2-chloroethyl)amino]ethoxy-2,3-dihydro-2,3-dimesyloxy- 1H-cyclopent[a]anthracene-6,11-dione,
9-[2-bis(2-chloroethyl)amino]ethoxy-2,3-dihydro-2,3-dimesyloxy- 1H-cyclopent[a]anthracene-6,11-dione,
2,3-dihydro-2,3-dimesyloxy-4-hydroxymethyl-1H-benz[e] inden-6,9-dione carbamate,
2,3-dihydro-2,3-dimesyloxy-4-hydroxymethyl-1H-benz[e] inden-6,9-dione N-methylcarbamate,
2,3-dihydro-2,3-dimesyloxy-4-hydroxymethyl-1H-7-methoxy-8-methyl-benz[e]inden- 6,9-dione carbamate,
2,3-dihydro-2,3-dimesyloxy-4-hydroxymethyl-1H-cyclopent[a]-anthracene- 6,11-dione-carbamate,
2,3-dihydro-2,3-dimesyloxy-4-hydroxymethyl-1H-cyclopent[a]-anthracene- 6,9-dione N-methylcarbamate,
2,3-dihydro-2,3-dimesyloxy-4-hydroxymethyl-8-methoxy-1H-cyclopent[a]anthracene- 6,11-dione carbamate,
2,3-dihydro-2,3-dimesyloxy-4-hydroxymethyl-8-methoxy-1H-cyclopent[a]anthracene- 6,11-dione N-methylcarbamate, and
2,3-dihydro-2,3-dimesyloxy-4-hydroxymethyl-9-methoxy-1H-cyclopent[a]anthracene- 6,11-dione N-methylcarbamate.

EXAMPLE 21

3-Azido-4-[2-N,N-bis(2-chloroethyl1)amino]ethoxy-2,3-dihydro-2-mesyloxy-1H-cyclo pent[a]anthracene-6,11-dione: A mixture of 4-[2-bis(2-chloroethyl)amino]ethoxy-2,3-dihydro-2,3-dihydroxy- 1H-cyclopent[a]anthracene-6,11-dione (270 mg, 0.58 mmol) and methanesulfonyl chloride (266 mg, 2.32 m mol) in pyridine (5 mL) is stirred in an ice-bath for 1 hour. The mixture is poured into ice water (50 mL), and extracted with CHCl$_3$ (30 mL×5). The combined CHCl$_3$ extracts are washed with H$_2$O dried (Na$_2$SO$_4$), and evaporated to dryness. The TLC (SiO$_2$, C$_6$C$_5$CH$_3$/EtOAc, 4:1 v/v) shows that there is only one reaction product, 2,3-Dihydro-2,3-cis-di-mesyloxy-1H-cyclopent[a]anthracene- 6,11-dione. The crude intermediate is obtained as a syrup $^1$H NMR (CDCl$_3$): δ2.99–3.13 (6H, m 3×N—CH$_2$—), 3.19 and 3.23 (each 3H, s, 2×Me), 3.44–3.72 (4H, 2×CH$_2$—Cl), 4.00–4.15 (2H, s, O—CH$_2$—), 4.21–4.39 (2H, m, 1—CH$_2$), 5.18–5.33 (1H, m, H-2), 6.22 (1H, d, J$_{2,3}$=5.48 Hz, H-3), 7.67 (1H, s, H-5), 7.72–8.27 (4H, m, Ar—H).

The above crude intermediate is dissolved in DMF (5mL), and LiN3 (200 mg) is added. The mixture is stirred at room temperature for 1 hour, diluted with ice-water (30 mL), and then extracted with CHCl$_3$ (30 mL×4). The organic extracts are combined and washed with H$_2$O, dried (Na$_2$SO$_4$), evaportated in vacuo to dryness to give crude 3-azido-4-[2-N,N-bis(2-chloroethyl)amino] ethoxy-2,3-dihydro-2-mesyloxy-1H-cyclopent[a] anthracene-6,11-dione, 232 mg (70%) as a syrup. The TLC (SiO$_2$, toluene/ethyl acetate 9:1 v/v) of the residue shows that there is only one product. The crude product is used directly in the next step without further purification. However, a small amount of pure compound can be obtained by chromatography on a silica gel column using toluene/ethyl acetate (1:9 v/v) as the eluent. IR (KBr): 2150 cm$^{-1}$ (N$_3$), 1690 cm$^{-1}$ $^{(c=o)}$, Ms: m/z 567. $^1$H NMR (CDCl$_3$): δ2.98–3.25 (6H, m, 3×N—CH$_2$), 3.10 (3H, s, Me), 3.51–3.66 (4H, t, J=6.04 Hz, 2×CH$_2$—Cl), 3.86–3.94 (2H, m, 1—CH$_2$), 4.35 (2H, t, J=6.04 Hz, O—CH$_2$—), 5.27–5.34 (2H, m, H-2, H-3), 7.77 (1H, s, H-5), 7.73–8.32 (4H, m, Ar—H).

By following the same procedure, the following compounds are prepared:
3-Azido-4-[2-bis(2-chloroethyl)amino]ethoxy-2,3-dihydro-2-mesyloxy- 1H-benz[e]inden-6,9-dione,
3-azido-4-[2-bis(2-hydroxyethyl)amino]ethoxy-2,3-dihydro-2-mesyloxy- 1H-benz [e]inden-6,9-dione,
3-azido-4-[2-bis(2-chloroethyl)amino]ethoxy-2,3-dihydro-2-mesyloxy- 7-methoxy-8-methyl-1H-benz[e]inden-6,9-dione,
3-azide-4-[2-bis(2-chloroethyl)amino]ethoxy-2,3-dihydro-7,8-dimethoxy- 2-mesyloxy-1H-benz[e]inden-6,9-dione,
3-azido-4-[2-bis(2-chloroethyl)amino]ethoxy-2,3-dihydro-2-mesyloxy- 8-methoxy-1H-cyclopent[a]anthracene-6,11-dione, 3-azido-4-[2-bis(2-hydroxyethyl)amino]ethoxy-2,3-dihydro-2-mesyloxy- 8-methoxy-1H-cyclopent[a]anthracene-6,11-dione, 3-azido-7-[2-bis(2-chloroethyl)amino]ethoxy-2,3-dihydro-2-mesyloxy- 1H-cyclopent[a]anthracene-6,11-dione, 3-azido-8-[2-bis(2-chloroethyl)amino]ethoxy-2,3-dihydro-2-mesyloxy- 1H-cyclopent[a]anthracene-6,11-dione, 3-azido-9-[2-N,N-bis(2-chloroethyl)amino]ethoxy-2,3-dihydro-2-mesyloxy- 1H-cyclopent[a]anthracene-6,11-dione, 3-azido-10-[2-N,N-bis(2-chloroethyl)amino]ethoxy-2,3-dihydro- 2-mesyloxy-1H-cyclopent[a]anthracene-6,11-dione, 3-azido-2,3-dihydro-4-hydroxymethyl-2-mesyloxy-1H-benz[e]inden- 6,9-dione carbamate, 3-azido-2,3-dihydro-4-hydroxymethyl-2-mesyloxy-1H-benz[e]inden-6,9-dione N-methylcarbamate, 3-azido-2,3-dihydro-4-hydroxymethyl-2-mesyloxy-1H-7-methoxy- 8-methyl-benze[e]inden-6,9-dione carbamate, 3-azido-2,3-dihydro-4-hydroxymethyl-2-mesyloxy-7,8-dimethoxy- 1H-benz[e]inden-6,9-dione carbamate, 3-azido-2,3-dihydro-7,8-dimethoxy-4-hydroxymethyl-2-mesyloxy- 1H-benz[e]inden-6,9-dione N-methylcarbamate, 3-azido-2,3-dihydro-4-hydroxymethyl-2-mesyloxy-1H cyclopent[a]anthracene-6,11-dione carbamate, 3-azido-2,3-dihydro-4-hydroxymethyl-2-mesyloxy-8-methoxy1H-cyclopent[a]anthracene- 6,11-dione carbamate, and 3-azido-2,3-dihydro-4-hydroxymethyl-2-mesyloxy-9-methoxy-1H-cyclopent[a]anthracene- 6,11-dione N-methylcarbamate.

EXAMPLE 22

2,3-Aziridino-4-[2-N,N-bis (2-chloroethyl)amino]ethoxy-2,3-dihydro-1H-cyclopent[a]anthracene-6,11-dione: To a mixture of 3-azido-4-[2-bis(2-chloroethyl)amino]ethoxy-2,3-dihydro- 2-mesyloxy-1H-cyclopent[a]anthracene-6,11-dione (120 mg, 0.21 mmol), $Et_3N$ (0.7 mL), in THF (7 mL) containing $H_2O$ (0.7 mL) is added triphenyl-phosphine (130 mg, 0.5 m mol). The reaction mixture is stirred at room temperature for 1.5 hours, and then diluted with EtOAc 30 mL). The solution is washed with $H_2O$ (15 mL×3), dried ($NaSO_4$), and evaporated in vacuo to dryness. The residue is chromatographed over a silica gel colum (2×30 cm) using EtOAc as the eluent to give 2,3-aziridino-4-[2-bis(2-chloroethyl)amino]ethoxy- 2,3-dihydro-1H-cyclopent[a]anthracene-6,11-dione, 45 mg (42%), mp 105°–106° C. (dec) ($Et_2$). $^1H$ NMR ($CDCl_3$): $\delta 1.26$ (1H, brs, NH), 3.08–3.24 (6H, m, H-2, H-3, 2× $CH_2$—Cl), 3.51–4.67 (7H, m, Ha-1, 3×$CH_2$—N), 3.83 (1H, d, J=19.3 Hz, Hb-1), 4.30 (2H, t, J=5.49 Hz, N—$CH_2$—$CH_2$—O), 7.64 (1H, s, H-5), 7.69– 8.69 (4H, m, Ar—H). Anal. Calc'd for $C_{23}H_{22}Cl_2N_2O_3$: C, 62.03; H, 4.98; N, 6.29; Cl, 15.92. Found: C, 62.03; H, 4.91; N, 6.10; Cl, 15.71.

By following the same procedure, the following compounds are prepared:

7-amino-2,3-aziridino-4-[2-bis(2-chloroethyl)amino] ethoxy- 2,3-dihydro-8-methyl-1H-benz[e]inden-6,9-dione, 7-amino-4-[2-bis(2-chloroethyl)amino]ethoxy-2,3-dihydro-8-methyl-2,3-N-methylaziridino-1H-benz[e]inden-6,9-dione, 7-amino-2,3-aziridino-4-[2-bis(2-hydroxyethyl)amino] ethoxy- 2,3-dihydro-8-methyl-1H-benz[e]inden-6,9-dione, 2,3-aziridino-4-[2-bis(2-chloroethyl)amino]ethoxy- 2,3-dihydro-7-methoxy-8-methyl-1H-benz[e]inden6,9-dione, 4-[2-bis(2-chloroethyl)amino]ethoxy-2,3-dihydro-7-methoxy- 8-methyl-2,3-N-methylaziridino-1H-benz[e]inden-6,9dione, 2,3-aziridino-4-[2-bis(2-chloroethyl)amino]ethoxy7-cyano-2,3-dihydro-8-methyl-1H-benz[e]inden-6,9-dione, 2,3-aziridino-4-[2-bis(2-chloroethyl)amino]ethoxy-2,3-dihydro- 7-ethyleneimino-8-methyl-1H-benz[e]inden-6,9dione, 2,3-aziridino-4-[2-bis(2-chloroethyl)amino]ethoxy-2,3-dihydro- 7-propargylamino-8-methyl-1H-benz[e]inden-6,9dione, 2,3-aziridino-4-[2-bis(2-chloroethyl)amino]ethoxy-2,3-dihydro- 7-tetrafurfurylamino-8-methyl-1-H-benz[e]inden-6,9-dione, 7-amino-2,3-aziridino-4-hydroxymethyl-2,3-dihydro-8-methyl-1H-benz[e]inden- 6,9-dione carbamate 7-amino-2,3-aziridino-4-hydroxymethyl-2,3-dihydro-8-methyl-1H-benz[e]inden-6,9-dione N-methylcarbamate, 7-amino-4-hydroxymethyl-2,3-dihydro-8-methyl-2,3-N-methyl-aziridino-1H-benz[e]inden- 6,9-dione, 7-amino-4-hydroxymethyl-2,3-dihydro-8-methyl-2,3-N-methyl-aziridino-1H-benz[e]inden- 6,9-dione N-methylcarbamate, 2,3-aziridino-4-hydroxymethyl-2,3-dihydro-7-methoxy-8-methyl- 1H-benz[e]inden-6,9-dione carbamate, 2,3-aziridino-4-hydroxymethyl-2,3-dihydro-7-methoxy-8-methyl- 1H-benz[e]inden-6,9-dione N-methylcarbamate, 2,3-dihydro-4-hydroxymethyl-7-methoxy-8-methyl-2,3-N-methyl -aziridino- 1H-benz[e]inden-6,9-dione, 2,3-aziridino-7-cyano-2,3-dihydro-4-hydroxymethyl-8-methyl-1H-benz[e]inden- 6,9-dione carbamate, 2,3-aziridino-2,3-dihydro-4-hydroxymethyl-7-ethyleneimino-8-methyl- 1H-benz[e]inden-6,9-dione carbamate, 2,3-aziridino-2,3-dihydro-4-hydroxymethyl-7-propargylamino-8-methyl-1H-benz[e]inden-6,9-dione carbamate, 2,3-aziridino-2,3-dihydro-4-hydroxymethyl-7-tetrafurfurylamino-8-methyl- 1H-benz[e]inden-6,9-dione carbamate, 2,3-aziridino-4-[2-bis(2-chloroethyl)amino]ethoxy-2,3-dihydro- 1H-cyclopent[a]anthracene-6,11-dione,

[2-bis(2-chloroethyl)amino]ethoxy-2,3-dihydro-1H-2,3-N-methylaziridino-cyclopent[a]anthracene- 6,11-dione, 2,3-aziridino-4-[2-bis(2-chloroethyl)amino]ethoxy-7-methoxy-2,3-dihydro- 1H-cyclopent[a]anthracene-6,11-dione, 4-[2-bis(2-chloroethyl)amino]ethoxy-7-methoxy-2,3-dihydro-2,3-N-methylaziridino-1H-cyclopent[a]anthracene-6, 11-dione, 2,3-aziridino-4-[2-bis(2-chloroethyl)amino]ethoxy-8-methoxy-2,3-dihydro-1H-cyclopent[a]anthracene-6,11-dione, 2,3-aziridino-4-[2-bis(2-chloroethyl)amino]ethoxy-9-methoxy-2,3-dihydro- 1H-cyclopent[a]anthracene-6,11-dione, 2,3-aziridino-7-[2-bis(2-chloroethyl)amino]ethoxy-2,3-dihydro- 1H-cyclopent[a]anthracene-6,11-dione, 7-[2-bis(2-chlorethyl)amino]ethoxy-2,3-dihydro-1H-2,3-N-methyl-aziridino-cyclopent[a] anthracene-6,11-dione, 2,3-aziridine-8-[2-bis(2-chloroethyl)amino]ethoxy-2,3-dihydro- 1H-cyclopent[a]anthracene-6,11-dione, 2,3-aziridino-9-[2-bis(2-chloroethyl)amino]ethoxy-2,3-dihydro- 1H-cyclopent[a]anthracene-6,11-dione, 2,3-aziridino-10-[2-bis(2-chloroethyl )amino]ethoxy-2,3-dihydro-1H-cyclopent[a]anthracene- 2,3-aziridino-4-[2-bis(2-hydroxyethyl)amino]ethoxy-2,3-dihydro- 1H-cyclopent [a]anthracene-6,11-dione, 2,3-aziridino-7-[2-bis (2-hydroxyethyl)amino]ethoxy-2,3-dihydro- 1H-cyclopent [a]anthracene-6,11-dione, 2,3-aziridino-8-[2-bis (2-hydroxyethyl)amino]ethoxy-2,3-dihydro- 1H-cyclopent [a]anthracene-6,11-dione, 2,3-aziridino-2,3-dihydro-4-hydroxymethyl-1H-cyclopent[a]-anthracene- 6,11-dione carbamate,
2,3-aziridino-2,3-dihydro-4-hydroxymethyl-1H-cyclopent[a]-anthracene- 6,11-dione N-methylcarbamate,
2,3-dihydro-4-hydroxymethyl-2,3-N-methylaziridino-1H-cyclopen[a]-anthracene- 6,11-dione carbamate,
2,3-aziridino-2,3-dihydro-4-hydroxymethyl-7-methoxy-1H-cyclopent[a]anthracene- 6,11-dione carbamate,
2,3-aziridino-2,3-dihydro-4-hydroxymethyl-8-methoxy-1H-cyclopent[a]anthracene- 6,11-dione carbamate,
2,3-aziridino-2,3-dihydro-4-hydroxymethyl-8-methoxy-1H-cyclopent[a]anthracene- 6,11-dione N-methylcarbamate,
2,3-aziridino-2,3-dihydro-4-hydroxymethyl-9-methoxy-1H-cyclopent[a]anthrcene-6,11-dione carbamate,
2,3-dihydro-4-hydroxymethyl-10-methoxy-2,3-N-methyl-aziridino-1 H-cyclopent[a]anthracene-6,11-dionecarbamate,
2,3-dihydro-4-hydroxymethyl-7-methoxy-2,3-N-methylaziridino-1H-cyclopent[a]anthracene-6,11-dione carbamate,
2,3-dihydro-4-hydroxymethyl-7-methoxy-2,3-N-methylaziridino-1H-cyclopent[a]anthracene-6,11-dione N-methylcarbamate,
2,3-dihydro-4-hydroxymethyl-8-methoxy-2,3-N-methylaziridino-1H-cyclopent[a]anthracene-6,11-dione carbamate, and
2,3-dihydro[4]hydroxymethyl-8-methoxy-2,3-N-methylaziridino-1H-cyclopent[a]anthracene-6,11-dione N-methylcarbamate.

Biological Activity

Compounds of the invention show antitumor activity. The antitumor activity of the representative cyclopentanthraquinone derivatives is compared with Mitomycin C, m-AMSA and adriamycin. The $IC_{50}$ values of the representative cyclopentanthraquinone derivatives for cell growth inhibition are listed in Table I. It is shown that cyclopentanthraquinone derivatives bearing an aziridine-ring at C2–C3 but without a mustard side-chain at $C_4$ (compound IIa, 2,3-aziridino-2,3-dihydro-1H-cyclopent[a]anthracene-6,11-dione), exhibit less activity against L1210 cell growth. On the other hand, a cyclopentanthraquinone derivative bearing a mustard side-chain at C-4 but without an aziridine-ring (compound IIb, -4-[ 2-bis(2-chloroethyl)amino]ethoxy-2,3-dihydro-1H-cyclopent[a]anthracene-6,11-dione) is shown to have significant antitumor activity against L1210 cell growth with $IC_{50}$ value of 0.29 μM. It is interesting to note that a compound bearing both aziridine-ring and mustard side-chain (compound IIc, 2,3-aziridino-4-[2-bis(2-chloroethyl)amino]-ethoxy-2, 3-dihydro-1H-cyclopent[a]anthracene-6,11-dione) exhibits much greater antitumor activity than that of IIa and IIb with $IC_{50}$ value of 0.064 μM.

Both compounds IIb and IIc are also shown to have significant antitumor activity against human leukemic HL-60 and MT4 cell growth in vitro. Compound IIc is half as active as m-AMSA against MT4 cell growth and as potent as m-AMSA against human leukemic HL-60 cell growth Preliminary studies show that compounds IIb and IIc produce an increase in life-span (ILS) at doses of 5 mg/kg, i.p., QD×5 of 36% in mice inoculated i.p. with L1210 cells (Table II).

TABLE I

The in vitro antitumor activity of cyclopent-anthraquinone derivatives.

| Compound | $IC_{50}$ (μM) for Cell Growth Inhibition | | |
| --- | --- | --- | --- |
|  | L1210 | HL-60 | MT4 |
| IIa | 9.09 | ND | ND |
| IIB | 0.29 | 0.18 | 0.11 |
| IIC | 0.064 | 0.075 | 0.069 |
| Mit-C | 0.005 | ND | ND |
| m-AMSA | 0.004 | 0.08 | 0.034 |
| Adriamycin | 0.02 | 0.03 | ND |

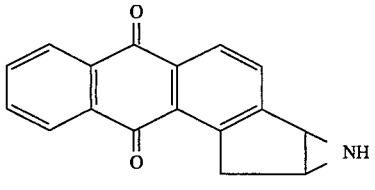

IIa

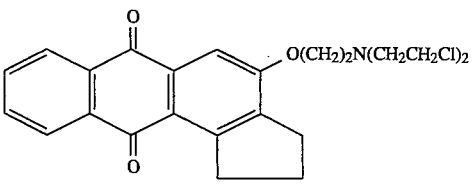

IIb

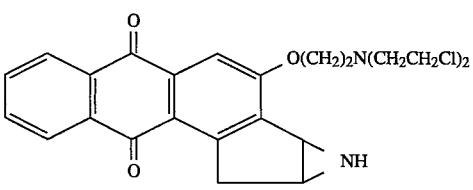

IIc

TABLE II

The effect of cyclopentanthraquinone derivatives against L1210 in mice.

| Compound | Dose (mg/kg) QD, i.p. | day 4 AWC (g) | day 7 AWC (g) | survival time | | | AST | % ILS* | N/T |
| --- | --- | --- | --- | --- | --- | --- | --- | --- | --- |
| control |  | +2.0 | / | 6 6 | 7 7 | 7 | 6.6 |  | 0/5 |
| Mit-C | 20 x1 | +1.0 | +2.0 | 11 |  |  | 11.0 | 67 | 0/1 |
|  | 2.5 x5 | +1.0 | −0.3 | 11 | 13 | 14 | 12.7 | 92 | 0/3 |
|  | 5.0 x5 | −2.0 | / | 6t | 6t | 6t |  |  | 0/3 |
| IIb | 20 x1 | −2.5 | +0.5 | 9 |  |  | 9.0 | 36 | 0/1 |
|  | 2.5 x5 | +0.3 | +1.0 | 9 | 9 | 9 | 9.0 | 36 | 0/3 |
|  | 5.0 x5 | −0.3 | +0.7 | 9 | 9 | 9 | 9.0 | 36 | 0/3 |
| IIc | 20 x1 | −2.5 | +1.5 | 9 |  |  | 9.0 | 36 | 0/1 |
|  | 2.5 x5 | +0.3 | +1.5 | 9 | 9 | 9 | 9.0 | 36 | 0/3 |

TABLE II-continued

The effect of cyclopentanthraquinone derivatives against L1210 in mice.

| Compound | Dose (mg/kg) QD, i.p. | day 4 AWC (g) | day 7 AWC (g) | survival time | | | AST | % ILS* | N/T |
|---|---|---|---|---|---|---|---|---|---|
| | 5.0 x5 | −0.3 | +1.7 | 9 | 9 | 9 | 9.0 | 36 | 0/3 |

*Increase in lifespan of 25% or greater is considered to be significant.
Mice dying of toxicity (t) not included in AST evaluation.

References

1. Carter et al., *Current Status and New Developments*; Academic Press; New York, 1979.
2. Moore, et al., *Science*, 1977; vol. 197, p. 527.
3. Thomasz, et al., *Biochemistry*, 1981; Vol. 20, p. 5056.
4. Thomasz, et al., *Science*, 1971; Vol. 235, p. 1204.
5. Archer, et al., *Ann. Rev, Pharmacol. Toxicology.*, 1985; Vol. 25, p. 485.
6. Watanabe, et al., *J, Med. Chem.*, 1989; Vol. 32, p. 1594.
7. Brown, et al., *J, Chem. Soc.*, 1950; p. 3634.
8. Know, et al., *Org. Prepns, and Proceds. Int.*, 1977; vol. 9, p. 285.
10 McCasland et al., *J, Org. Chem.*, 1962; Vol. 28, p. 894.
10. Caine et al., *Tetrahedron Lett.*, 1983; Vol. 24, p. 1353.
11. Kinoshita et al., *J. Med. Chem.*, 1971; vol. 14, p. 103.
12. Archer et al., *J. Med. Chem.*, 1988; Vol. 31, p. 254.

What is claimed is:

1. A compound having the structure:

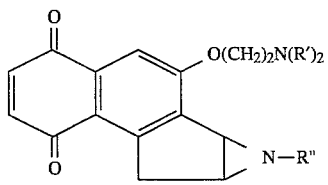

wherein R' is H or a C1–C5 alkyl, hydroxyalkyl or haloalkyl group, wherein the halo atom is F, Cl, Br or I, and R" is H or a C1–C9 alkyl group.

2. A compound having the structure:

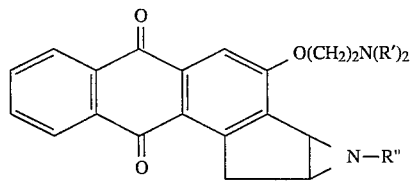

wherein R' is H or a C1–C5 alkyl, hydroxyalkyl or haloalkyl group, wherein the halo atom is F, Cl, Br or I, and R" is H or a C1–C9 alkyl group.

3. The compound of claim 2 having the structure:

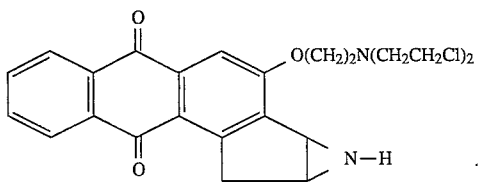

* * * * *